(12) United States Patent
Gschliesser et al.

(10) Patent No.: US 11,389,474 B2
(45) Date of Patent: Jul. 19, 2022

(54) PHARMACEUTICAL COMPOSITIONS FOR DELIVERY OF PEPTIDE

(71) Applicant: ANYA BIOPHARM INC., Taipei (CN)

(72) Inventors: Siegfried Gschliesser, Taipei (CN); Bhushan Dhruvkumar Desai, Thane (IN)

(73) Assignee: ANYA BIOPHARM INC., Taipei (CN)

(*) Notice: Subject to any disclaimer, the term of this patent is extended or adjusted under 35 U.S.C. 154(b) by 0 days.

(21) Appl. No.: 16/324,008

(22) PCT Filed: Sep. 19, 2018

(86) PCT No.: PCT/IB2018/057209
§ 371 (c)(1),
(2) Date: Feb. 7, 2019

(87) PCT Pub. No.: WO2019/058273
PCT Pub. Date: Mar. 28, 2019

(65) Prior Publication Data
US 2020/0121796 A1    Apr. 23, 2020

(30) Foreign Application Priority Data
Sep. 21, 2017    (IN) .............................. 201711033555

(51) Int. Cl.
| | |
|---|---|
| *A61K 33/24* | (2019.01) |
| *A61K 9/48* | (2006.01) |
| *A61K 38/29* | (2006.01) |
| *A61K 38/31* | (2006.01) |
| *A61K 47/02* | (2006.01) |
| *A61K 47/18* | (2017.01) |
| *A61K 47/20* | (2006.01) |
| *A61K 47/22* | (2006.01) |
| *A61K 47/26* | (2006.01) |
| *A61K 38/25* | (2006.01) |
| *A61K 38/26* | (2006.01) |
| *A61K 38/28* | (2006.01) |

(52) U.S. Cl.
CPC ............ *A61K 33/24* (2013.01); *A61K 9/4808* (2013.01); *A61K 38/25* (2013.01); *A61K 38/26* (2013.01); *A61K 38/28* (2013.01); *A61K 38/29* (2013.01); *A61K 38/31* (2013.01); *A61K 47/02* (2013.01); *A61K 47/18* (2013.01); *A61K 47/20* (2013.01); *A61K 47/22* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 2006/0252686 A1* | 11/2006 | Fine ..................... | A61K 31/155 514/493 |
| 2007/0087957 A1 | 4/2007 | Kidron | |
| 2014/0056953 A1 | 2/2014 | Foeger et al. | |

FOREIGN PATENT DOCUMENTS

| | | |
|---|---|---|
| EP | 1800675 B1 | 5/2011 |
| EP | 3006045 B1 | 4/2017 |
| WO | 2016/055550 A1 | 4/2016 |
| WO | WO-2016055550 A1 * | 4/2016 ............. A61K 38/27 |

OTHER PUBLICATIONS

Drugbank entry for Teriparatide DB06285, downloaded Sep. 14, 2020 (Year: 2020).*
Drugbank entry for Insulin DB00030, downloaded Sep. 14, 2020 (Year: 2020).*
Drugbank entry for GLP-1 DBCAT001327, downloaded Sep. 14, 2020 (Year: 2020).*
PubChem entry for vanadium (V) oxide PubChem CID 14814, downloaded Sep. 14, 2020 (Year: 2020).*
Entry for manganese chloride on mindat.org, downloaded Sep. 14, 2020 (Year: 2020).*
PubChem entry for Vitamin A PubChem CID 445354, downloaded Sep. 14, 2020 (Year: 2020).*
PubChem entry for Vitamin E PubChem CID 14985, downloaded Sep. 14, 2020 (Year: 2020).*
International Search Report dated Dec. 14, 2018, for corresponding International Patent Application No. PCT/IB2018/057209.
Written Opinion dated Dec. 14, 2018, for corresponding International Patent Application No. PCT/IB2018/057209.
Renukuntla J et al., Int J Pharm. Apr. 15, 2013.
Laffleur F et al.; Thiomers: promising platform for macromolecular drug delivery; Future Med Chem, 2012, 4(17), 2205-2216.

* cited by examiner

*Primary Examiner* — Christina Bradley
(74) *Attorney, Agent, or Firm* — Sughrue Mion, PLLC

(57) ABSTRACT

The present invention relates to a pharmaceutical composition including: a pharmaceutically effective amount of at least one peptide; and a pharmaceutically acceptable amount of a combination of: (a) at least one metal in form of any or a combination of a salt thereof and a complex thereof; and (b) at least one reducing agent, wherein, the at least one metal is selected from any or a combination of: vanadium, chromium and manganese, and wherein the combination of (a) at least one metal in form of any or a combination of a salt and a complex and (b) at least one reducing agent affords protection, at least in part, to the at least one peptide from proteolytic degradation upon ingestion thereof.

12 Claims, 1 Drawing Sheet

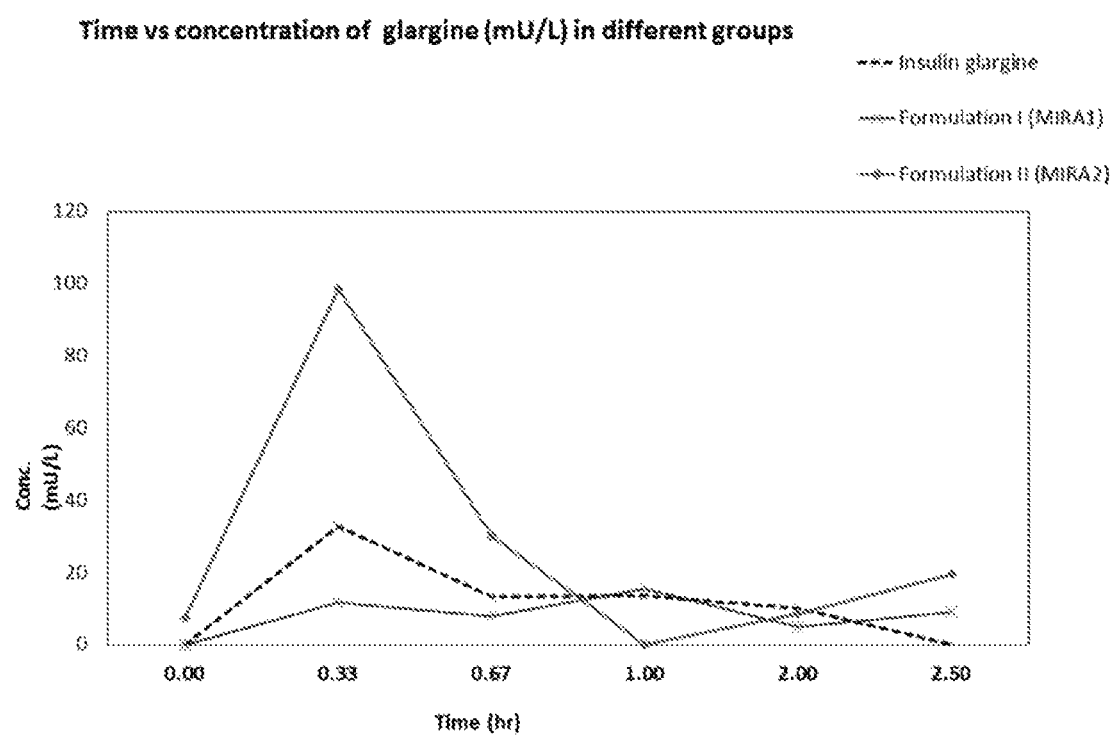

PHARMACEUTICAL COMPOSITIONS FOR DELIVERY OF PEPTIDE

This application is a National Stage Application under 35 U.S.C. § 371 of PCT International Application No. PCT/IB2018/057209, filed Sep. 19, 2018, which takes priority from Indian Provisional Application Number IN 201711033555, filed Sep. 21, 2017, all of which is herein incorporated in its entirety.

TECHNICAL FIELD

The present disclosure generally relates to the field of pharmaceuticals. More specifically, the present invention relates to a pharmaceutical composition including a peptide in combination with a metal salt/complex and a reducing agent to afford protection, at least in part, to the peptide from proteolytic degradation upon ingestion thereof.

BACKGROUND

Background description includes information that may be useful in understanding the present invention. It is not an admission that any of the information provided herein is prior art or relevant to the presently claimed invention, or that any publication specifically or implicitly referenced is prior art.

Proteins and polypeptides are used as therapeutic agent(s), diagnostic agent(s) and the like from a long time, and even today their numbers are growing rapidly. However, their complete potential has not been realized yet as their application is limited only to parenteral injection.

Oral route is a simple, convenient and most preferred route for administration of a therapeutic agent. However, degradation of peptides in gastrointestinal tract prevents their absorption as an intact entity. Thus, enzymatic degradation in the gastrointestinal tract and poor permeability through the epithelial cells are the main reasons for their low oral bioavailability.

Different approaches have been proposed over a period of time to improve oral bioavailability of such proteins and polypeptides, such as use of a myriad of absorption enhancers and protease inhibitors like soybean trypsin inhibitor, aprotinin, bowman birk inhibitor, bacitracin, camostat mesilate and amastatin (Renukuntla J et al., *Int J Pharm.* 2013, 447, 75-93 and US application US20070087957A1). However, none of these protease inhibitors succeeded as an additive in application of polypeptide drug delivery at a commercially scale, as they are toxic and may exhibit several side-effects.

Few example of protease inhibitors utilized for delivery of peptides are as follow: a) Soybean (trypsin inhibitor)—it is one of the widely accepted allergens and number of people suffering from soya has been increasing steadily since 1980s limiting its utilization (Moroz L A et al., *N Engl J Med* 1980, 302, 1126-8; Foucard T et al., Allergy, 1999, 54, 261-5; Ramesh S, *Clin Rev Allergy Immunol.* 2008, 34, 217-30). It causes immediate allergic reactions such as coughing, sneezing, running nose, hives, diarrhea, facial swelling, shortness of breath, swollen tongue, difficulty in swallowing, lowered blood pressure, excessive perspiration, fainting, anaphylactic shock and even death, b) Bowman (birk inhibitor)—it is a soybean derivative with high oral bioavailability even in the absence of an absorption enhancer, however, it is reported to exert unwanted systemic protease inhibition (systemic inhibition of serine proteases such as plasmin that may increases the risk of thrombosis) after oral intake. Further, bowman may also results in formation of antibodies against itself (Wan X S et al., *Nutr Cancer,* 2002, 43, 167-73), c) Aprotinin—it is known to cause anaphylaxis at a rate of 1:200 in first-time use (Mandy A M et al., 2004, 93, 842-58), and is also reported to be associated with a risk of acute renal failure, myocardial infarction, heart failure, stroke and encephalopathy in a patient suffering from cardiac disorder/surgery (Mangano D T et al., *N Engl J Med,* 2006, 354, 353-65).

As these protease inhibitors are associated with potential health risks, it is commonly accepted that utilization of these protease inhibitors should be avoided. Apart from facing these limitations, they are associated with high manufacturing cost, heterogeneity, regulatory hurdles, challenges as to achieving selective inhibition, and requirement of high doses for effective activity (Renukuntla J et al., *Int J Pharm.* 2013, 447) making its utilization non-viable. Other protease inhibitors such as bacitracin (antibiotic activity), camostat mesilate (effective in treating pancreatitis) or amastatin (antibacterial activity) are also associated with similar side-effects (Renukuntla J et al., *Int J Pharm* 2013, 447, 75-93 and US publication US20070087957A1).

European patent EP3006045B1 discloses a combination of trace elements such as copper or zinc with a pharmaceutically acceptable reducing agent, optionally in combination with a mucosal absorption enhancer that results in a surprisingly high and advantageous oral bioavailability of different peptide or protein drugs. However, copper and zinc are associated with many metabolic pathways in mammals, and hence, utilization thereof for a long-term therapy may results in negative interactions.

There is, therefore, a need in the art to develop simple, safe, efficient and cost-effective pharmaceutical compositions that can deliver peptide while providing protection, at least in part, to the peptides from proteolytic degradation upon ingestion thereof. The present disclosure satisfies the existing needs, as well as others and alleviates the shortcomings of the traditional pharmaceutical compositions and delivery techniques.

OBJECTS OF THE INVENTION

An object of the present disclosure is to provide a pharmaceutical composition that can overcomes the deficiencies associated with the prior-art reported compositions.

Another object of the present disclosure is to provide a pharmaceutical composition for effective delivery of peptide.

Another object of the present disclosure is to provide a pharmaceutical composition for oral delivery of peptide.

Another object of the present disclosure is to provide a pharmaceutical composition that provides protection, at least in part, to the peptide to be ingested from proteolytic degradation.

Another object of the present disclosure is to provide a pharmaceutical composition that increases oral bioavailability of peptide.

Another object of the present disclosure is to provide a pharmaceutical composition that is safe.

Another object of the present disclosure is to provide a pharmaceutical composition that is cost-effective to manufacture.

Another object of the present disclosure is to provide a pharmaceutical composition that is easy to prepare.

Another object of the present disclosure is to provide a pharmaceutical composition that exhibits long shelf-life.

SUMMARY

The present disclosure generally relates to the field of pharmaceuticals. More specifically, the present invention relates to a pharmaceutical composition including a peptide in combination with a metal salt/complex and a reducing agent to afford protection, at least in part, to the peptide from proteolytic degradation upon ingestion thereof.

An aspect of the present disclosure provides a pharmaceutical composition including: a pharmaceutically effective amount of at least one peptide; and a pharmaceutically acceptable amount of a combination of: (a) at least one metal in form of any or a combination of a salt thereof and a complex thereof; and (b) at least one reducing agent, wherein, the at least one metal is selected from any or a combination of: vanadium, chromium and manganese, and wherein the combination of (a) at least one metal in form of any or a combination of a salt and a complex and (b) at least one reducing agent affords protection, at least in part, to the at least one peptide from proteolytic degradation upon ingestion thereof.

In an embodiment, the at least one metal is vanadium and wherein the pharmaceutical composition includes any or a combination of the salt of vanadium and the complex of vanadium in an amount ranging from about 0.01 mg to about 15 mg per unit dose. In an embodiment, the any of the salt of vanadium and the complex of vanadium is selected independently from a group including: vanadium (V) oxide, sodium vanadate, vanadium sulfate, vanadyl sulfate, vanadium biguanide, bis(maltolato)oxavandium (IV), vanadium acetate, vanadyl picolinate and vanadyl citrate. In an embodiment, the at least one metal is chromium and wherein the pharmaceutical composition includes any or a combination of the salt of chromium and the complex of chromium in an amount ranging from about 0.02 mg to about 0.5 mg per unit dose. In an embodiment, the any of the salt of chromium and the complex of chromium is selected independently from a group including: chromium picolinate, chromium polynicotinate, chromium nicotinate, chromium chloride and chromium acetate. In an embodiment, the at least one metal is manganese and wherein the pharmaceutical composition includes any or a combination of the salt of manganese and the complex of manganese in an amount ranging from about 0.1 mg to about 10 mg per unit dose. In an embodiment, the any of the salt of manganese and the complex of manganese is selected independently from a group including: manganese gluconate, manganese sulfate, potassium permanganate and manganese chloride.

In an embodiment, the at least one peptide has molecular weight of equal to or less than 60 kDa. In an embodiment, the at least one peptide is selected from a group including: insulin, an insulin analog, insulin lispro, insulin PEGlispro, insulin aspart, insulin glulisine, insulin glargine, insulin detemir, NPH insulin, insulin degludec, B29K(N(ε)hexadecanedioyl-γ-L-Glu) A14E B25H desB30 human insulin, B29K(N(ε)octadecanedioyl-γ-L-Glu-OEG-OEG) desB30 human insulin, B29K(N(ε)octadecanedioyl-γ-L-Glu) A14E B25H desB30 human insulin, B29K(N(ε)eicosanedioyl-γ-L-Glu) A14E B25H desB30 human insulin, B29K(N(ε)octadecanedioyl-γ-L-Glu-OEG-OEG) A14E B25H desB30 human insulin, B29K(N(ε)eicosanedioyl-γ-L-Glu-OEG-OEG) A14E B25H desB30 human insulin, B29K(N(ε)hexadecanedioyl-γ-L-Glu) A14E B16H B25H desB30 human insulin, B29K(N(ε)eicosanedioyl-γ-L-Glu-OEG-OEG) A14E B16H B25H desB30 human insulin, B29K(N(ε)octadecanedioyl) A14E B25H desB30 human insulin, GLP-1, a GLP-1 analog, an acylated GLP-1 analog, a diacylated GLP-1 analog, semaglutide, liraglutide, exenatide, lixizenatide, a dual agonist of the GLP-1 receptor and the glucagon receptor, amylin, an amylin analog, pramlintide, a somatostatin analog, octreotide, lanreotide, pasireotide, goserelin, buserelin, leptin, a leptin analog, metreleptin, peptide YY, a peptide YY analog, glatiramer, leuprolide, teriparatide, abaloparatide, tetracosactide, corticorelin, etelcalcetide, elcatonin, desmopressin, human growth hormone, a human growth hormone analog, a glycopeptide antibiotic, a glycosylated cyclic or polycyclic nonribosomal peptide antibiotic, vancomycin, teicoplanin, telavancin, bleomycin, ramoplanin, decaplanin, bortezomib, cosyntropin, chorionic gonadotropin, menotropin, sermorelin, luteinizing-hormone-releasing hormone, somatropin, calcitonin, calcitonin-salmon, pentagastrin, oxytocin, neseritide, anakinra, enfuvirtide, pegvisomant, dornase alfa, lepirudin, anidulafungin, eptifibatide, interferon alfacon-1, interferon alpha-2a, interferon alpha-2b, interferon beta-1a, interferon beta-1 b, interferon gamma-1 b, peginterferon alfa-2a, peginterferon alfa-2b, peginterferon beta-1a, fibrinolysin, vasopressin, aldesleukin, epoetin alfa, darbepoetin alfa, epoetin beta, epoetin delta, epoetin omega, epoetin zeta, filgrastim, interleukin-11, cyclosporine, glucagon, urokinase, viomycin, thyrotropin-releasing hormone, leucine-enkephalin, methionine-enkephalin, substance P, adrenocorticotropic hormone, parathyroid hormone, and pharmaceutically acceptable salts thereof.

In an embodiment, the at least one peptide and the at least one metal in form of any or a combination of a salt thereof and a complex thereof are present in physically separated form in the pharmaceutical composition. In an embodiment, the at least one peptide and the at least one metal in form of any or a combination of a salt thereof and a complex thereof are present in separate compartments. In an embodiment, the pharmaceutical composition is present in form of any of capsule-in-capsule and tablet-in-capsule.

In an embodiment, the at least one reducing agent is selected from any or a combination of ascorbic acid, reduced glutathione, cysteine, uric acid, reducing sugar, glyceraldehyde, α-tocopherol, vitamin A, α-lipoic acid, dihydro-α-lipoic acid, glucose, galactose, lactose, maltose, thiol-bearing compound, a thiomer and pharmaceutically acceptable salts thereof. In an embodiment, the pharmaceutical composition includes the at least one reducing agent in an amount ranging from about 1 mg to about 1000 mg per unit dose.

In an embodiment, the pharmaceutical composition further includes at least one absorption or permeation enhancer and wherein the at least one absorption or permeation enhancer is present in an amount ranging from about 10 mg to about 1000 mg per unit dose. In an embodiment, the pharmaceutical composition is formulated as any of a solid oral dosage form and a liquid oral dosage form, with proviso that when said pharmaceutical composition is formulated as the liquid oral dosage form, the pharmaceutical composition includes water in an amount of less than about 5% v/v.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 illustrates a graph depicting conc. vs. time profile of insulin glargine (mU/L) from different formulations, in accordance with an embodiment of the present disclosure.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms as used herein are shown below. To the extent a term used in a claim is not defined below, it should be given the broadest definition persons in the pertinent art have given that term as reflected in printed publications and issued patents at the time of filing.

The present disclosure generally relates to the field of pharmaceuticals. More specifically, the present invention relates to a pharmaceutical composition including a peptide in combination with a metal salt/complex and a reducing agent to afford protection, at least in part, to the peptide from proteolytic degradation upon ingestion thereof.

Serine Proteases are ubiquitously found in eukaryotes and cleave peptide bonds in which the main catalytic triad is serine, histidine, and aspartic acid. The Serine proteases specified in the present invention include trypsin, chymotrypsin, carboxypeptidase B and aminopeptidase M, which are responsible for bodily physiological functions, specifically digestion (proteolytic degradation) i.e. hydrolyzation of peptide bonds and amino acids. The present disclosure aims to provide pharmaceutical composition(s) including a peptide in combination with a metal salt/complex and a reducing agent to afford protection, at least in part, to the peptide from proteolytic degradation upon ingestion thereof.

Accordingly, an aspect of the present disclosure provides a pharmaceutical composition including: a pharmaceutically effective amount of at least one peptide; and a pharmaceutically acceptable amount of a combination of: (a) at least one metal in form of any or a combination of a salt thereof and a complex thereof; and (b) at least one reducing agent, wherein, the at least one metal is selected from any or a combination of: vanadium, chromium and manganese, and wherein the combination of (a) at least one metal in form of any or a combination of a salt and a complex and (b) at least one reducing agent affords protection, at least in part, to the at least one peptide from proteolytic degradation upon ingestion thereof.

In an embodiment, the at least one metal is vanadium and wherein the pharmaceutical composition includes any or a combination of the salt of vanadium and the complex of vanadium in an amount ranging from about 0.01 mg to about 5 mg per unit dose. In an embodiment, the any of the salt of vanadium and the complex of vanadium is selected independently from a group including: vanadium (V) oxide, sodium vanadate, vanadium sulfate, vanadyl sulfate, vanadium biguanide, bis(maltolato)oxavandium (IV), vanadium acetate, vanadyl picolinate and vanadyl citrate. In an embodiment, the at least one metal is chromium and wherein the pharmaceutical composition includes any or a combination of the salt of chromium and the complex of chromium in an amount ranging from about 0.02 mg to about 0.5 mg per unit dose. In an embodiment, the any of the salt of chromium and the complex of chromium is selected independently from a group including: chromium picolinate, chromium polynicotinate, chromium nicotinate, chromium chloride and chromium acetate. In an embodiment, the at least one metal is manganese and wherein the pharmaceutical composition includes any or a combination of the salt of manganese and the complex of manganese in an amount ranging from about 0.1 mg to about 10 mg per unit dose. In an embodiment, the any of the salt of manganese and the complex of manganese is selected independently from a group including: manganese gluconate, manganese sulfate, potassium permanganate and manganese chloride.

In an embodiment, the at least one peptide has molecular weight of equal to or less than 60 kDa. In an embodiment, the at least one peptide is selected from a group including: insulin, an insulin analog, insulin lispro, insulin PEGlispro, insulin aspart, insulin glulisine, insulin glargine, insulin detemir, NPH insulin, insulin degludec, B29K(N(ε)hexadecanedioyl-γ-L-Glu) A14E B25H desB30 human insulin, B29K(N(ε)octadecanedioyl-γ-L-Glu-OEG-OEG) desB30 human insulin, B29K(N(ε)octadecanedioyl-γ-L-Glu) A14E B25H desB30 human insulin, B29K(N(ε)eicosanedioyl-γ-L-Glu) A14E B25H desB30 human insulin, B29K(N(ε) octadecanedioyl-γ-L-Glu-OEG-OEG) A14E B25H desB30 human insulin, B29K(N(ε)eicosanedioyl-γ-L-Glu-OEG-OEG) A14E B25H desB30 human insulin, B29K(N(ε)eicosanedioyl-γ-L-Glu-OEG-OEG) A14E B16H B25H desB30 human insulin, B29K(N(ε)hexadecanedioyl-γ-L-Glu) A14E B16H B25H desB30 human insulin, B29K(N(ε) eicosanedioyl-γ-L-Glu-OEG-OEG) A14E B16H B25H desB30 human insulin, B29K(N(ε)octadecanedioyl) A14E B25H desB30 human insulin, GLP-1, a GLP-1 analog, an acylated GLP-1 analog, a diacylated GLP-1 analog, semaglutide, liraglutide, exenatide, lixizenatide, a dual agonist of the GLP-1 receptor and the glucagon receptor, amylin, an amylin analog, pramlintide, a somatostatin analog, octreotide, lanreotide, pasireotide, goserelin, buserelin, leptin, a leptin analog, metreleptin, peptide YY, a peptide YY analog, glatiramer, leuprolide, teriparatide, abaloparatide, tetracosactide, corticorelin, etelcalcetide, elcatonin, desmopressin, human growth hormone, a human growth hormone analog, a glycopeptide antibiotic, a glycosylated cyclic or polycyclic nonribosomal peptide antibiotic, vancomycin, teicoplanin, telavancin, bleomycin, ramoplanin, decaplanin, bortezomib, cosyntropin, chorionic gonadotropin, menotropin, sermorelin, luteinizing-hormone-releasing hormone, somatropin, calcitonin, calcitonin-salmon, pentagastrin, oxytocin, neseritide, anakinra, enfuvirtide, pegvisomant, dornase alfa, lepirudin, anidulafungin, eptifibatide, interferon alfacon-1, interferon alpha-2a, interferon alpha-2b, interferon beta-1a, interferon beta-1 b, interferon gamma-1 b, peginterferon alfa-2a, peginterferon alfa-2b, peginterferon beta-1a, fibrinolysin, vasopressin, aldesleukin, epoetin alfa, darbepoetin alfa, epoetin beta, epoetin delta, epoetin omega, epoetin zeta, filgrastim, interleukin-11, cyclosporine, glucagon, urokinase, viomycin, thyrotropin-releasing hormone, leucine-enkephalin, methionine-enkephalin, substance P, adrenocorticotropic hormone, parathyroid hormone, and pharmaceutically acceptable salts thereof.

In an embodiment, the at least one peptide and the at least one metal in form of any or a combination of a salt thereof and a complex thereof are present in physically separated form in the pharmaceutical composition. In an embodiment, the at least one peptide and the at least one metal in form of any or a combination of a salt thereof and a complex thereof are present in separate compartments. In an embodiment, the pharmaceutical composition is present in form of any of capsule-in-capsule and tablet-in-capsule.

In an embodiment, the at least one reducing agent is selected from any or a combination of ascorbic acid, reduced glutathione, cysteine, uric acid, reducing sugar, glyceraldehyde, α-tocopherol, vitamin A, α-lipoic acid, dihydro-α-lipoic acid, glucose, galactose, lactose, maltose, thiol-bearing compound, a thiomer and pharmaceutically acceptable salts thereof. In an embodiment, the pharmaceutical composition includes the at least one reducing agent in an amount ranging from about 1 mg to about 1000 mg per unit dose.

In an embodiment, the pharmaceutical composition further includes at least one absorption or permeation enhancer and wherein the at least one absorption or permeation enhancer is present in an amount ranging from about 10 mg to about 1000 mg per unit dose. In an embodiment, the pharmaceutical composition is formulated as any of a solid oral dosage form and a liquid oral dosage form, with proviso that when said pharmaceutical composition is formulated as the liquid oral dosage form, the pharmaceutical composition includes water in an amount of less than about 5% v/v.

In an embodiment, the peptide is any peptide or protein that is suitable to be used as a therapeutic or a diagnostic agent. In an embodiment, the peptide is a linear peptide or a cyclic peptide. In an embodiment, peptide is a modified or derivatized peptide, such as a PEGylated peptide or a fatty acid acylated peptide or a fatty diacid acylated peptide and the likes. Peptides can be free of histidine residues and/or free of cysteine residues. Generally, it is preferred that the peptide is water-soluble, particularly at neutral pH (i.e., at about pH 7) and has at least one serine protease cleavage site, i.e., the peptide comprises one or more amino acid residue(s) amenable or prone to cleavage by a serine protease (particularly an intestinal serine protease, such as trypsin, chymotrypsin, aminopeptidase, carboxypeptidase, elastase and/or dipeptidyl-4-peptidase) and the likes.

In an embodiment, peptide is selected from any or a combination of insulin (preferably human insulin), an insulin analog such as but not limited to a long acting basal insulin analog, a protease stabilized long acting basal insulin analog, insulin lispro, insulin PEGlispro, the insulin derivative like A14E, B25H, B29K(N(eps)octadecanedioyl-gGlu-OEG-OEG), desB30 human insulin, insulin aspart, insulin glulisine, insulin glargine, insulin detemir, NPH insulin, insulin degludec, and the insulin analogs/derivatives described in US application number US20140056953A1, GLP-1, a GLP-1 analog (acylated GLP-1 analog or a diacylated GLP-1 analog), semaglutide, liraglutide, exenatide, lixizenatide, a dual agonist of the GLP-1 receptor and the glucagon receptor, amylin, an amylin analog, pramlintide, a somatostatin analog (octreotide, lanreotide, or pasireotide), goserelin (goserelin acetate), buserelin, leptin, a leptin analog (metreleptin), peptide YY (PYY), a PYY analog, glatiramer (glatiramer acetate), leuprolide, teriparatide, abaloparatide, tetracosactide, corticorelin, etelcalcetide, elcatonin, desmopressin, human growth hormone (hGH), a human growth hormone analog, a glycopeptide antibiotic (a glycosylated cyclic or polycyclic nonribosomal peptide such as vancomycin, teicoplanin, telavancin, bleomycin, ramoplanin, or decaplanin), bortezomib, cosyntropin, chorionic gonadotropin, menotropin, sermorelin, luteinizing-hormone-releasing hormone (LHRH, also referred as gonadotropin-releasing hormone), somatropin, calcitonin (calcitonin-salmon), pentagastrin, oxytocin, neseritide, anakinra, enfuvirtide, pegvisomant, dornase alfa, lepirudin, anidulafungin, eptifibatide, interferon alfacon-1, interferon alpha-2a, interferon alpha-2b, interferon beta-1a, interferon beta-1b, interferon gamma-1b, peginterferon alfa-2a (pegylated interferon alfa-2a), peginterferon alfa-2b (pegylated interferon alfa-2b), peginterferon beta-1a (pegylated interferon beta-1a), fibrinolysin, vasopressin, aldesleukin, epoetin alfa, darbepoetin alfa, epoetin beta, epoetin delta, epoetin omega, epoetin zeta, filgrastim, interleukin-11, cyclosporine, glucagon, urokinase, viomycin, thyrotropin-releasing hormone (TRH), leucine-enkephalin, methionine-enkephalin, substance P (CAS no. 33507-63-0), adrenocorticotropic hormone (ACTH), parathyroid hormone (PTH), and pharmaceutically acceptable salts thereof. However, any other peptide molecule, as known to or appreciated by a person skilled in the art, can be utilized to serve its intended purpose, as laid in the present disclosure, without departing from the scope and spirit of the present invention.

In an embodiment, for human subject peptide is selected from any or a combination of endogenous peptide such as insulin or glucagon and the likes. In a preferred embodiment, a human isoform of the corresponding peptide that is recombinantly expressed or chemically synthesized is used. However, any other human isoform peptide, as known to or appreciated by a person skilled in the art, can be utilized to serve its intended purpose, as laid in the present disclosure, without departing from the scope and spirit of the present invention.

In an embodiment, peptide is insulin analog. In an embodiment, the insulin analog is selected from any or a combination of insulin Detemir, insulin glargine, insuline degludec, and other insulin analogs derived from human, porcine, fish. However, any other insulin analog/derivative, as known to or appreciated by a person skilled in the art, can be utilized to serve its intended purpose, as laid in the present disclosure, without departing from the scope and spirit of the present invention.

In an embodiment, a mixture of two or more peptides can be used. In an embodiment, a mixture of human insulin and a GLP-1 agonist (e.g. liraglutide, semaglutide, exenatideor lixizenatide) is used. However, mixture of any two or more peptides (including the peptides discussed above), as known to or appreciated by a person skilled in the art, can be utilized to serve its intended purpose, as laid in the present disclosure, without departing from the scope and spirit of the present invention.

In an embodiment, the at least one peptide exhibits molecular weight of equal to or less than 60 kDa. In an embodiment, the at least one peptide exhibits molecular weight of equal to or less than 40 kDa. In an embodiment, the at least one peptide exhibits molecular weight of equal to or less than 30 kDa. In an embodiment, the at least one peptide exhibits molecular weight of equal to or less than 20 kDa. In an embodiment, the at least one peptide exhibits molecular weight of equal to or less than 10 kDa. In an embodiment, the at least one peptide exhibits molecular weight ranging from about equal to or greater than 300 Da to about equal to or less than 50 kDa. However, peptide with any range of molecular weight, as known to or appreciated by a person skilled in the art, can be utilized to serve its intended purpose, as laid in the present disclosure, without departing from the scope and spirit of the present invention.

In an embodiment, the molecular weight of the at least one peptide can be determined by any method such as mass spectrometry (electrospray ionization mass spectrometry (ESI-MS) or matrix-assisted laser desorption/ionization mass spectrometry (MALDI-MS)), gel electrophoresis (polyacrylamide gel electrophoresis using sodium dodecyl sulfate (SDS-PAGE)), hydrodynamic methods (gel filtration chromatography or gradient sedimentation), or static light scattering (e.g., multi-angle light scattering (MALS), known to or appreciated by a person skilled in the art, to serve its intended purpose, as laid in the present disclosure, without departing from the scope and spirit of the present invention.

In an embodiment, the at least one metal is vanadium and wherein the pharmaceutical composition includes any or a combination of the salt of vanadium and the complex of vanadium. In an embodiment, the any or a combination of the salt of vanadium and the complex of vanadium is selected independently form a group including vanadium (IV), vanadium (V) and vanadium as vanadyl (V02) salt complex and vanadium as anion in Vanadate salt/complex. In an embodiment, vanadium salt and vanadium complexes is selected from any or a combination of vanadium (V) oxide, vanadium pentoxide, vanadium dioxide, sodium vanadate, vanadium sulphate, vanadyl sulfate, sodium metavanadate, vanadium tetrachloride, vanadium (V) oxychloride, vanadium oxytrichloride, vanadyl chloride, vanadium trichloroxo, ammonium vanadate, ammonium vanadium oxide, vanadium monosulfide, vanadium sulfide, Vanadium (IV) Chloride, Vanadiu biguanide, (bis)maltolato)oxavandium (IV), Vanadium acetate, vanadyl picolinate, vanadyl citrate and the likes. In preferred embodiment, the salt and the complex of vanadium is vanadium (V). It is advantageous to use salts and complex of vanadium (V) because of their good aqueous solubility and better oxidation state stability in comparison to the salts and complexes of vanadium (IV). In an embodiment, salts and complexes of vanadium are vanadium (IV) salt and/or complex, wherein vanadium is a part of an anion as vanadate, or a part of a cation as Vanadyl. However, any or a combination of salts and complexes of vanadium, as known to or appreciated by a person skilled in the art, can be utilized to serve its intended purpose, as laid in the present disclosure, without departing from the scope and spirit of the present invention.

In an embodiment, the pharmaceutical composition includes any or a combination of the salt of vanadium and the complex of vanadium in an amount ranging from about 0.01 mg to about 15.0 mg per unit dose.

In an embodiment, the salt of chromium and the complex of chromium are selected preferably from chromium (III) salt and/or complex. In an embodiment, any or a combination of the salt of chromium and the complex of chromium is selected from chromium picolinate, chromium chloride, chromium nicotinate, chromium polynicotinate, chromium acetate, trivalent chromium, high-chromium yeast, chromium 2-pyridine-carboxylate, chromium tripicolinate, 2-pyridinecarboxylic acid-chromium salt, tris(picolinato) chromium and the likes. In an embodiment, the salt of chromium and the complex of chromium are selected more preferably from chromium picolinate, chromium polynicotinate, chromium nicotinate, chromium chloride, chromium acetate and the likes. However, any or a combination of salts and complexes of chromium, as known to or appreciated by a person skilled in the art, can be utilized to serve its intended purpose, as laid in the present disclosure, without departing from the scope and spirit of the present invention.

In an embodiment, the pharmaceutical composition includes any or a combination of the salt of chromium and the complex of chromium in an amount ranging from about 0.01 mg to about 50 mg per unit dose, preferably from about 0.02 mg to about 0.5 mg per unit dose.

In an embodiment, the any or a combination of the salt of manganese and the complex of manganese is selected from manganese (II) salt and/or complex, manganese (III) salt and/or complex, manganese as permanganate (V02) salt and/or complex. In an embodiment, any or a combination of the salts of manganese and the complexes of manganese is selected from any or a combination of manganese (II) sulfate (MnSO4), manganese (II) chloride (MnCl2), manganese (III) acetate, potassium permanganate, sodium permanganate, manganese gluconate and the likes. In an embodiment, the salt of manganese and the complex of manganese are selected more preferably from manganese (III) salt and/or complex. In an embodiment, the manganese (III) salts and/or complexes are selected from any or a combination of manganese gluconate, manganese sulfate, manganese chloride and the likes. However, any or a combination of salts and complexes of manganese, as known to or appreciated by a person skilled in the art, can be utilized to serve its intended purpose, as laid in the present disclosure, without departing from the scope and spirit of the present invention.

In an embodiment, the pharmaceutical composition includes any or a combination of the salt of manganese and the complex of manganese in an amount ranging from about 0.01 mg to about 50 mg per unit dose, preferably from about 0.1 mg to about 10 mg per unit dose.

In an embodiment, any or a combination of salts and complexes of vanadium, chromium and manganese, as known to or appreciated by a person skilled in the art, can be utilized to serve its intended purpose, as laid in the present disclosure, without departing from the scope and spirit of the present invention.

In an embodiment, the salts and the complexes of vanadium are preferred over the salts and the complexes of chromium and manganese as the salts and the complexes of vanadium significantly improves the oral bioavailability of the peptides. In an embodiment, the salts and the complexes of chromium are preferred over the salts and the complexes of manganese. In an embodiment, the use of the salts and the complexes of chromium are also advantageous as they are less toxic. In an embodiment, the use of the salts and the complexes of manganese are advantageous over salts of vanadium and chromium as the salts and complexes of manganese are safe to human even at high dose.

In an embodiment, the reducing agent is selected from any or a combination of ascorbic acid (preferably an ascorbate such as sodium ascorbate), reduced glutathione (GSH), cysteine, uric acid, a reducing sugar (a reducing monosaccharide, such as glucose, glyceraldehyde or galactose, or a reducing disaccharide, such as lactose or maltose), mannitol, α-tocopherol, vitamin A, α-lipoic acid, dihydro-α-lipoic acid (DHLA), a thiol-bearing compound, a thiomer (includes thiomers Laffleur F et al., *Future Med Chem,* 2012, 4, 2205-16), and the likes. In an embodiment, a mixtures of two or more reducing agents, can be used, preferably, ascorbate and reduced glutathione. However, any or a combination of reducing agent(s), as known to or appreciated by a person skilled in the art, can be utilized to serve its intended purpose, as laid in the present disclosure, without departing from the scope and spirit of the present invention.

In an embodiment, the pharmaceutical composition includes a reducing agent in an amount ranging from about 1.0 mg to about 1000 mg per unit dose, preferably from about 50 mg to about 500 mg per unit dose.

In an embodiment, the pharmaceutical composition further includes at least one absorption enhancer (or permeation enhancer). It should be appreciated that the terms "absorption enhancer" and "permeation enhancer" as interchangeably and synonymously used herein throughout the present disclosure encompass within its meaning, absorption enhancers and permeation enhancers, as known to or appreciated by a person skilled in the pertinent art. In an embodiment, administration of least one absorption or permeation enhancer improves or facilitates the mucosal absorption of the peptide in the gastrointestinal tract, especially, if the peptide is having large size. In an embodiment, the at least one absorption or permeation enhancer is selected from any or a combination of zwitter-ionic absorption enhancer or a non-ionic absorption enhancer. In an embodiment, the at least one absorption enhancer is selected from any or a combination of C8-20 alkanoyl carnitine (preferably lauroyl carnitine, myristoylcarnitine or palmitoyl carnitine; e.g., lauroyl carnitine chloride, myristoyl carnitine chloride or paimitoyi carnitine chloride), salicylic acid (preferably a salicylate, e.g., sodium salicylate), a salicylic acid derivative (such as 3-methoxysalicylicacid, 5-methoxysalicylic acid, or homovanillic acid, a C8-20 alkanoic acid (preferably a C8-20 alkanoate, more preferably a caprate, a caprylate, a myristate, a palmitate, or a stearate, such as sodium caprate, sodium caprylate, sodiummyristate, sodium palmitate, or sodium stearate), citric acid (preferably a citrate such as sodium citrate), a fatty acid acylatedamino acid (any of the fatty acid acylated amino acids disclosed in US patent application US20140056953A1 without being limited thereto, sodium lauroyl alaninate, N-dodecanoyl-L-alanine, sodiumlauroyl asparaginate, N-dodecanoyl-L-asparagine, sodium lauroyl aspartic acid, N-dodecanoyl-L-aspartic acid, sodiumlauroyl cysteinate, N-dodecanoyl-L-cysteine, sodium lauroyl glutamic acid, N-dodecanoyl-L-glutamic acid, sodium lauroylglutaminate, N-dodecanoyl-L-glutamine, sodium lauroyl glycinate, N-dodecanoyl-L-glycine, sodium lauroyl histidinate,N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-Lserine,sodium lauroyl threoninate, N-dodecanoyl-L-threonine, sodium lauroyl tryptophanate, N-dodecanoyl-L-tryptophane,sodium lauroyl tyrosinate, N-dodecanoyl-L-tyrosine, sodium lauroyl valinate, N-dodecanoyl-L-valine, sodiumlauroyl sarcosinate, N-dodecanoyl-L-sarcosine, sodium capric alaninate, N-decanoyl-L-alanine, sodium capric asparaginate,N-decanoyl-L-asparagine, sodium capric aspartic acid, N-decanoyl-L-aspartic acid, sodium capric cysteinate,N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine,sodium capric isoleucinate, N-decanoyl-L-isoleucine, sodium capric leucinate, N-decanoyl-L-leucine, sodium capric methioninate,N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-Lthreonine,sodium capric tryptophanate, N-decanoyl-L-tryptophane, sodium capric tyrosinate, N-decanoyl-L-tyrosine,sodium capric valinate, N-decanoyl-L-valine, sodium capric sarcosinate, N-decanoyl-L-sarcosine, sodium oleoyl sarcosinate,sodium N-decylleucine, sodium stearoyl glutamate (Amisoft HS-11 P), sodium myristoyl glutamate (Amisoft MS-11), sodium lauroyl glutamate (Amisoft LS-11), sodium cocoyl glutamate (Amisoft CS-11), sodiumcocoyl glycinate (Amilite GCS-11), sodium N-decyl leucine, sodium cocoyl glycine, sodium cocoyl glutamate, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamicacid, N-dodecanoyl-L-glutamic acid, sodium lauroyl glutaminate, N-dodecanoyl-L-glutamine, sodium lauroyl glycinate,N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methinoninate, N-dodecanoyl-L-methionine, sodium lauroyl phenylalaninate, N-dodecanoyl-L-phenylalanine, sodium lauroyl prolinate, N-dodecanoyl-L-proline, sodium lauroyl serinate, N-dodecanoyl-L-serine, sodium lauroyl threoninate, N-dodecanoyl-L-threonine, sodiumlauroyl tryptophanate, N-dodecanoyl-L-tryptophane, sodium lauroyl tyrosinate, N-dodecanoyl-L-tyrosine, sodiumlauroyl valinate, N-dodecanoyl-L-valine, N-dodecanoyl-L-sarcosine, sodium capric alaninate, N-decanoyl-L-alanine, sodiumcapric asparaginate, N-decanoyl-L-asparagine, sodium capric aspartic acid, N-decanoyl-L-aspartic acid, Sodium capric cysteinate, N-decanoyl-L-cysteine, sodium capric glutamic acid, N-decanoyl-L-glutamic acid, sodium capricglutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine,sodium capric prolinate, N-decanoyl-L-proline, sodium capric serinate, N-decanoyl-L-serine, sodium capric threoninate,N-decanoyl-L-threonine, sodium capric tryptophanate, N-decanoyl-L-tryptophane, sodium capric tyrosinate, N-decanoyl-L-tyrosine, sodium capric valinate, N-decanoyl-L-valine, sodium capric sarcosinate, sodium oleoyl sarcosinate, and the pharmaceutically acceptable salts of any of the aforementioned compounds such as C8-20 alkanoyl sarcosinate (a lauroyl sarcosinate, such as sodium lauroyl sarcosinate) or one of the 20 standard proteinogenic α-amino acids that is acylated with a $C_{8-20}$ alkanoic acid), an alkylsaccharide ($C_{1-20}$ alkylsaccharide such as $C_{8-10}$ alkylpolysaccharide like Multitrope™ 1620-LQ-(MV), or n-octyl-beta-D-glucopyranoside, or n-dodecyl-beta-D-maltoside), a cyclodextrine (α-cyclodextrin, β-cyclodextrin, γ-cyclodextrin, methyl-β-cyclodextrin, hydroxypropyl β-cyclodextrin, or sulfobutylether β-cyclodextrin), sodium N-[8-(2-hydroxybenzoyl)amino]caprylate (SNAC), a thiomer (includes the thiomers that are disclosed in Laffleur F et al., *Future Med Chem.* 2012, 4, 2205-16), a calcium chelating compound (ethylenediaminetetraacetic acid (EDTA), ethylene glycol tetraacetic acid (EGTA), sodium citrate, or polyacrylic acid), cremophor EL (Kolliphor E L; CAS no. 61791-12-6), chitosan, N,N,N-trimethyl chitosan, benzalkonium chloride, bestatin, cetylpyridinium chloride, cetyltrimethylammonium bromide, a $C_2$-20 alkanol (e.g., ethanol, decanol, lauryl alcohol, myristyl alcohol, or palmityl alcohol), a $C_{8-20}$ alkenol (e.g., oleyl alcohol), a $C_{8-20}$ alkenoic acid (e.g., oleic acid), dextran sulfate, diethyleneglycol monoethyl ether (transcutol), 1-dodecylazacyclo-heptan-2-one (Azone), ethyl caprylate, glyceryl monolaurate, lysophosphatidylcholine, menthol, a $C_{8-20}$ alkylamine, a $C_{8-20}$ alkenylamine (e.g., oleylamine), phosphatidylcholine, a poloxamer, polyethylene glycol monolaurate, polyoxyethylene, polypropylene glycol monolaurate, a polysorbate (polysorbate 80), a deoxycholate (sodium deoxycholate), sodium glycocholate, sodium glycodeoxycholate, sodium lauryl sulfate (SDS), a taurocholate (e.g., sodium taurocholate), a taurodeoxycholate (sodium taurodeoxycholate), sucrose laurate, a sulfoxide (a ($C_{1-10}$ alkyl), ($C_{1-10}$alkyl)-sulfoxide, such as, decyl methyl sulfoxide, or dimethyl sulfoxide), cyclopentadecalactone, 8-(N-2-hydroxy-5-chloro-benzoyl)-amino-caprylic acid (5-CNAC), dodecyl-2-N,N-dimethyl-amino propionate (DDAIP), D-α-tocopheryl polyethylene glycol-1000 succinate (TPGS), and pharmaceutically acceptable salts of the aforementioned compounds and the likes. In an embodiment, a mixture of any of two or more absorption enhancers, including the above-described absorption enhancers, can be used. However, any or a combination of absorption enhancer(s), as known to or appreciated by a person skilled in the art, can be utilized to serve its intended purpose, as laid in the present disclosure, without departing from the scope and spirit of the present invention.

In an embodiment, the pharmaceutical composition optionally includes an absorption or permeation enhancer in an amount ranging from about 10 mg to about 1000 mg per unit dose, preferably from about 50 mg to about 500 mg per unit dose.

In an embodiment, the pharmaceutical composition is constituted such that, if the pharmaceutical composition is added to ten milliliters of 5% HCl solution, it would neutralize the acid and generate a pH of higher than about 6. In an embodiment, the pharmaceutical composition is constituted such that, if the pharmaceutical composition is added to ten milliliters of aqueous solution, it would generate a pH ranges from 6 to 9.

In an embodiment, the pharmaceutical composition including: a pharmaceutically effective amount of at least one peptide exhibiting molecular weight of equal to or less than 50 kDa, at least any or a combination of the salt of vanadium and the complex of vanadium, at least one reducing agent, and optionally an absorption enhancer is administrated orally to affords protection, at least in part, to the at least one peptide from proteolytic degradation upon ingestion.

In an embodiment, the pharmaceutical composition including: a pharmaceutically effective amount of at least one peptide exhibiting molecular weight of equal to or less than 50 kDa, at least any or a combination of the salt of chromium and the complex of chromium, at least one reducing agent, and optionally an absorption enhancer is administrated orally to affords protection, at least in part, to the at least one peptide from proteolytic degradation upon ingestion.

In an embodiment, the pharmaceutical composition including: a pharmaceutically effective amount of at least one peptide exhibiting molecular weight of equal to or less than 50 kDa, at least any or a combination of the salt of manganese and the complex of manganese, at least one reducing agent, and optionally an absorption enhancer is administrated orally to affords protection, at least in part, to the at least one peptide from proteolytic degradation upon ingestion.

In an embodiment, the pharmaceutical composition further includes optionally any or a combination of one or more pharmaceutically acceptable excipients, such as but not limited to carriers, diluents, fillers, disintegrants, lubricating agents, binders, colorants, pigments, stabilizers, preservatives, antioxidants, and/or solubility enhancers. In an embodiment, the pharmaceutical composition, optionally, further includes one or more pharmaceutically acceptable additives such as vitamin E, histidine, microcrystallinecellulose (MCC), mannitol, starch, sorbitol and/or lactose. In an embodiment, the pharmaceutical compositions can be formulated by any techniques known to or appreciated by a person skilled in the art, to serve its intended purpose, as laid in the present disclosure, without departing from the scope and spirit of the present invention.

In an embodiment, the at least one solubility enhancers is selected from any or a combination of poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodexin, dihydroxypropyl-β-cyclodextrin, Sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate and the likes. However, any or a combination of solubility enhancer(s), as known to or appreciated by a person skilled in the art, can be utilized to serve its intended purpose, as laid in the present disclosure, without departing from the scope and spirit of the present invention.

In an embodiment, the pharmaceutical composition is formulated as dosage form for oral administration, preferably, peroral administration. In an embodiment, at least one peptide, at least one metal in form of any or a combination of a salt thereof and a complex thereof, at least one reducing agent and the optional absorption enhancer are administered orally.

In an embodiment, an oral pharmaceutical dosage form is selected from any or a combination of tablets (coated or uncoated tablets), capsules (soft gelatin capsules, hard gelatin capsules, HPMC capsules, or HPMCP capsules), a capsule-in-capsule, tablet-in-capsule, lozenges, troches, ovules, solutions, emulsions, suspensions, syrups, elixirs, powders and granules for reconstitution, dispersible powders and granules, medicated gums, chewing tablets, effervescent tablets, multi-particulate dosage forms and the likes. However, any or a combination of oral pharmaceutical dosage form(s), as known to or appreciated by a person skilled in the art, can be utilized to serve its intended purpose, as laid in the present disclosure, without departing from the scope and spirit of the present invention.

In an embodiment, the tablets may includes any or a combination of excipients such as but not limited to microcrystalline cellulose, lactose, sodium citrate, calcium carbonate, dibasic calcium phosphate, glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin, acacia, lubricating agents such as magnesium stearate, stearic acid, glyceryl behenate and talc. However, any or a combination of excipient(s), as known to or appreciated by a person skilled in the art, can be utilized to serve its intended purpose, as laid in the present disclosure, without departing from the scope and spirit of the present invention.

In an embodiment, the capsule may includes any or a combination of excipients such as but not limited to lactose, starch, a cellulose, or high molecular weight polyethylene glycols. However, any or a combination of excipient(s), as known to or appreciated by a person skilled in the art, can be utilized to serve its intended purpose, as laid in the present disclosure, without departing from the scope and spirit of the present invention.

In an embodiment, aqueous suspensions and/or elixirs, may includes any or a combination of excipients such as but not limited to sweetening or flavoring agents, coloring matter or dyes, emulsifying and/or suspending agents and diluents such as water, ethanol, propylene glycol and glycerin. However, any or a combination of excipient(s), as known to or appreciated by a person skilled in the art, can be utilized to serve its intended purpose, as laid in the present disclosure, without departing from the scope and spirit of the present invention.

In an embodiment, the pharmaceutical composition is formulated as any of a solid oral dosage form and a liquid oral dosage form, with proviso that when the pharmaceutical composition is formulated as the liquid oral dosage form, the pharmaceutical composition includes water in an amount of less than about 5% v/v, preferably less than about 3% v/v, more preferably less than about 1% v/v, even more preferably less than about 0.5% v/v, yet even more preferably less than about 0.1% v/v, and still more preferably free of water. In an embodiment, such liquid oral dosage form is particularly advantageous as they provide an improved shelf-stability. In an alternative embodiment, such liquid oral dosage form can be prepared shortly before administration, and prolonged storage periods should be avoided.

The amount of vanadium, chromium and/or managenese, utilized in accordance with embodiments of the present disclosure, is well below the recommended daily intake levels of these trace elements and can therefore be regarded as safe. Moreover, vanadium, chromium and/or managenese in combination with a reducing agent exert inhibitory effect on serine proteases in the gastrointestinal tract but do not show a systemic effect, which provides a further safety improvement as compared to the above-discussed protease inhibitors. Furthermore, vanadium, chromium or managenese as well as reducing agents such as ascorbate or reduced glutathione can be provided at considerably lower manufacturing costs than the above-discussed protease inhibitors that have previously been suggested for the oral delivery of peptide or protein drugs.

Typically, a physician will determine the actual dosage which will be most suitable for an individual subject. The specific dose level and frequency of dosage for any particular individual subject may be varied and will depend upon a variety of factors including the activity of the specific peptide or protein drug employed, the metabolic stability and length of action of that compound, the age, body weight, general health, sex, diet, mode and time of administration, rate of excretion, drug combination, the severity of the particular condition, and the individual subject undergoing therapy. The precise dose will ultimately be at the discretion of the attendant physician or veterinarian. The subject or patient to be treated, such as the subject in need of treatment or prevention, may be an animal (e.g., a non-human animal), a vertebrate animal, a mammal, a rodent (e.g., a guinea pig, a hamster, a rat, a mouse), murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is also envisaged that animals are to be treated which are economically or agronomically important. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

In an embodiment, at least one peptide, at least one metal in form of any or a combination of a salt thereof and a complex thereof, at least one reducing agent and the optional absorption enhancer can be administered simultaneously/concomitantly or sequentially. In an embodiment, in sequential administration, the at least one metal in form of any or a combination of a salt thereof and a complex thereof, at least one reducing agent can be administered first, followed by the administration of peptide and the optional absorption enhancer (e.g., at least about 5 min after the first administration, preferably about 5 min to about 3 hours after the first administration, more preferably about 10 min to about 1 hour after the first administration), which is particularly advantageous, if the peptide is insulin (human insulin). In an embodiment, at least one metal in form of any or a combination of a salt thereof and a complex thereof, at least one reducing agent and the optional absorption enhancer can be administered first, followed by the administration of the peptide (e.g., at least about 5 min after the first administration, preferably about 5 min to about 3 hours after the first administration, more preferably about 10 min to about 1 hour after the first administration), which is likewise advantageous, if the peptide is insulin (human insulin). In an embodiment, the at least one metal is selected from any or a combination of: vanadium, chromium and manganese.

In an embodiment, in simultaneous administration, the at least one metal in form of any or a combination of a salt thereof and a complex thereof, at least one reducing agent can be administered first, followed by the administration of peptide and the optional absorption enhancer is administered in the same pharmaceutical composition, or in two or more different/separate pharmaceutical compositions, or in two or more different/separate compartments of the same pharmaceutical dosage form. In an embodiment, the at least one metal is selected from any or a combination of: vanadium, chromium and manganese.

In an embodiment, the at least one peptide and the at least one metal in form of any or a combination of a salt thereof and a complex thereof are present in physically separated form in the pharmaceutical composition.

In an embodiment, a pharmaceutical dosage form includes at least two separate compartments which are physically separated from one another (e.g., through a physical separation layer). In an embodiment, the pharmaceutical dosage form includes a physical separation layer between the at least one peptide, the at least one metal in form of any or a combination of a salt thereof and a complex thereof. In an embodiment, the at least one peptide is present only in a first compartment, and the at least one metal in form of any or a combination of a salt thereof and a complex thereof is/are present only in a second compartment of the pharmaceutical dosage form. In an embodiment, the reducing agent is present either in the first compartment, or in the second compartment, or in both the first and the second compartment, or in a third compartment of the pharmaceutical dosage form. In an embodiment, the least one metal is selected from any or a combination of: vanadium, chromium and manganese.

In an embodiment, the pharmaceutical composition is present in the form of any of capsule-in-capsule and tablet-in-capsule pharmaceutical dosage form, the pharmaceutical composition including: at least one peptide having a molecular weight of equal to or less than about 50 kDa, which is present in a first compartment of the pharmaceutical dosage form; the at least one metal in form of any or a combination of a salt thereof and a complex thereof which is/are present in a second compartment of the pharmaceutical dosage form; and a reducing agent, which is present in the first compartment and/or the second compartment of the pharmaceutical dosage form.

In an embodiment, the invention provides a pharmaceutical dosage form (e.g., a multi-particulate dosage form) comprising: at least one peptide having a molecular weight of equal to or less than about 60 kDa, which is present in a first compartment of the pharmaceutical dosage form; a reducing agent, which is present in a second compartment of the pharmaceutical dosage form; and the at least one metal in form of any or a combination of a salt thereof and a complex thereof, which is/are present in a third compartment of the pharmaceutical dosage form. It an embodiment, the pharmaceutical dosage form is a capsule-in-capsule or a multi-particulate dosage form. In an embodiment, in a capsule-in-capsule dosage form, the bigger outer capsule (the content of which will be released first) contains the at least one metal in form of any or a combination of a salt thereof and a complex thereof and the reducing agent, and that the smaller inner capsule (the content of which will be released later) contains the peptide. In an embodiment, the least one metal is selected from any or a combination of: vanadium, chromium and manganese. In an embodiment, the dosage form is selected from any or a combination of release-modified dosage form (such as a dosage form (a capsule, multiparticulate or tablet) having an enteric coating), a dosage form (a capsule, multiparticulate or tablet) coated with Eudragit L30D55 or Eudragit FS30D, an acid resistant capsule such as HPMCP capsules (commercially known as AR Caps®) and the likes. However, any other dosage form, as known to or appreciated by a person skilled in the art, can be utilized to serve its intended purpose, as laid in the present disclosure, without departing from the scope and spirit of the present invention.

Example

The Serine proteases—trypsin, chymotrypsin, carboxypeptidase B and aminopeptidase M, which are responsible for proteolytic degradation of peptide bonds and amino acids were tested specifically for their oxidative inactivation by combination of metal ion(s) and reducing agent(s).

Enzyme Activity Assay:

The assay of enzymatic activity of each enzyme in the presence of its specific substrate was performed at a particular wavelength by using UV spectrophotometer, and it served as a negative control. The enzyme activity was calculated as:

$$\text{Units/mg solid} = \frac{\text{Units/ml enzyme}}{\text{mg solid/mg enzyme}}$$

Enzyme Inhibition Assay:

Incubation was performed with inhibitor of each enzyme, which served as a positive control.

Incubation with Metal Ion(s) and Reducing Agent(s):

Incubation of enzymes with combination of metal salt(s) and reducing agent(s) in microtitre 96 well plate was done for a specific period of time in presence of substrates to examine their oxidative inactivation. Inactivation of enzyme in presence of metal ion(s) and reducing agent(s) was compared with the original enzyme activity in the presence of substrate as a negative control and in the presence of inhibitor as a positive control.

pH Measurement:

The change in pH of enzymes after incubation with metal salt(s) and reducing agent(s) was monitored by Hanna combination pH electrode.

Zymogram:

The treated enzymes were subjected to zymography, which is an electrophoretic technique for detection of hydrolytic enzymes based on the substrate repertoire of enzyme i.e. substrate for the enzyme was embedded in the resolving gel during preparation of the acrylamide gel following which the digestion of substrate by enzyme was monitored.

Assay by Kits:

Assays by Protease Fluorescent detection kit and Trypsin Activity assay kit was performed to authenticate the inactivation.

Materials

Table 1A hereinbelow provides materials utilized for evaluating the efficacy of various metal salts and metal complexes, optionally, in combination with one or more reducing agents in effecting inhibition of serine protease enzyme(s).

TABLE 1A

| Sr. No | Enzymes | Substrates | Inhibitors | Metal Salts (tested) | Reducing Agents (tested) | Assay Kits | pH Activity |
|---|---|---|---|---|---|---|---|
| 1 | Human Trypsin | Nα-Benzoyl-L-arginine ethyl ester (BAEE) | 4-Amidinophenylmethane-sulfonyl fluoride hydrochloride (Serine Protease (inhibitor-for Trypsin/Chymotrypsin) | Copper Chloride Copper Carbonate Copper Sulphate Zinc Sulphate Zinc Chloride Zinc Acetate | Ascorbate Sodium Reduced Glutathione Uric Acid Mannitol Benzohydroxamic Acid Cysteine Piperine | Protease Fluorescent assay Kit Trypsin Activity Assay KIt | Hanna Combination pH electrode |
| | | Nα-Benzoyl-L-arginine-7-amido-4-methyl-coumarin hydrochloride | 3,4-Dichloro-isocoumarin (Serine Protease Inhibitor- for Trypsin/Chymotrypsin | Vanadium (IV) Sulphate Vanadium (V) oxide Sodium Vanadate Potassium Permanganate Manganese Glycerophosphate Manganese Gluconate Chromium | | | |
| 2. | Human Chymotrypsin | Ala-Ala-Phe-7-amido-4-methylcoumarin | 4-Amidinophenyl-methane-sulfonyl fluoride hydrochloride (Serine Protease (inhibitor-for Trypsin/Chymotrypsin) | Chloride Chromium Picolinate | Protease Fluorescent assay Kit | | |
| | | N-Benzoyl-L-tyrosine amidobenzoic acid sodium salt | 3,4-Dichloro-isocoumarin (Serine Protease Inhibitor- for Trypsin/Chymotrypsin | | | | |
| 3. | Human Carboxy-peptidase B | Hippuryl-Lys N-Benzoyl-L-tyrosine amidobenzoic acid | Ethylene-diaminetetra acetic acid disodium salt dihydrate | | | | |
| 4. | Porcine Aminopep-tidase M | L-Leucine-p-nitroanilide N-Succinyl-Ala-Ala-Pro-Phe-7-amido-4-methylcoumarin | 4.1 L-Leucinethiol, oxidized dihydrochloride | | | | |

Table 1B hereinbelow provides combinations of metal salts/metal complexes with reducing agent(s) evaluated for effecting inhibition of serine protease enzyme(s).

TABLE 1B

Combination of metal salts and complexes with reducing agents evaluated for inactivation of enzymes

| Sr. No. | Reducing agent (5 µM) | Metal Salt (1 mM/L) |
|---|---|---|
| 1. | Ascorbate sodium | Copper chloride/ascorbate sodium |
|  |  | Copper sulfate/ascorbate sodium |
|  |  | Zinc Sulfate'/ascorbate sodium |
|  |  | vanadium (IV) sulfate/ascorbate sodium |
|  |  | vanadium (V) oxide |
|  |  | Sodium Vanadate |
|  |  | Potassium Permanganate/ascorbate sodium |
|  |  | Manganese gluconate/ascorbate sodium |
|  |  | Chromium Picolinate/ascorbate sodium |
| 2. | Reduced Glutathione | Copper chloride/reduced glutathione |
|  |  | vanadium (IV) sulfate/reduced glutathione |
|  |  | vanadium (V) oxide/reduced glutathione |
|  |  | Sodium Vanadate/reduced glutathione |
|  |  | Manganese glycerophosphate/reduced glutathione |
|  |  | Chromium Chloride/reduced glutathione |
| 3. | Uric Acid | Copper sulfate/uric acid |
|  |  | Sodium Vanadate/uric acid |
|  |  | Manganese gluconate/uric acid |
|  |  | Chromium Picolinate/uric acid |
|  |  | Piperine/none |
| 4. | Mannitol | vanadium (IV) sulfate/mannitol |
|  |  | Zinc Sulfate'/mannitol |
|  |  | vanadium (IV) sulfate/mannitol |
|  |  | Manganese glycerophosphate/mannitol |
|  |  | Chromium Picolinate/mannitol |
| 5. | Benzohydroxamic Acid | Copper sulfate/benzohydroxamic acid |
|  |  | vanadium (IV) sulfate/benzohydroxamic acid |
|  |  | vanadium (V) oxide/benzohydroxamic acid |
|  |  | Sodium Vanadate/benzohydroxamic acid |
|  |  | Manganese glycerophosphate/benzohydroxamic acid |

Assay for Enzymatic Activity of Trypsin Using $N_\alpha$-Benzoyl-L-Arginine Ethyl Ester (BAEE)

200 units/ml Trypsin solution in cold HCl solution, and 0.25 mM BAEE substrate solution were prepared separately, and incubated. The above prepared solutions were mixed by inversion to form a reaction mixture and increase in absorbance at $A_{253}$ was recorded (usage of minimum 4 data points in 1 minute time period will be there) for blank solution (no enzyme) and test (reaction mixture) solution. The $A_{253}$/minute will be obtained using the maximum linear rate for both, blank & test solution.

Calculation for Trypsin in 3 ml Assay:

$$BAEE \text{ units/ml enzyme} = \frac{(\Delta A_{253}/\text{minute Test} - \Delta A_{253}/\text{minute Blank}) \times (df) \times (3)}{0.1 \times 0.808}$$

Where df=dilution factor, 3=total volume of assay for trypsin (in ml), 0.1=total volume of enzyme (in ml), 0.808=extinction coefficient of Nα Benzoyl L Arginine at 253 nm.

Determination of Inactivation of Trypsin in Presence of Inhibitors:

Trypsin (1 mM/L) was incubated with specific (known) inhibitors (provided in Table 1A), and combination of metal salts/reducing agents (provided in Table 2 hereinbelow) separately. Inactivation by inhibitors served as a positive control.

TABLE 2

Combinations of metal salts/complexes with reducing agents for inactivation of proteolytic enzymes

| Sr. No. | Reducing Agents Name | Conc. | Metal salts Name | Conc. |
|---|---|---|---|---|
| 1 | Ascorbate Sodium | 1 mM | Copper Chloride | 5 µM |
| 2 | Ascorbate Sodium | 1 mM | Copper Sulfate | 5 µM |
| 3 | Ascorbate Sodium | 1 mM | Zinc Sulfate | 5 µM |
| 4 | Ascorbate Sodium | 1 mM | Vanadium Sulfate | 5 µM |
| 5 | Ascorbate Sodium | 1 mM | Vanadium Oxide | 5 µM |
| 6 | Ascorbate Sodium | 1 mM | Sodium Vanadate | 5 µM |
| 7 | Ascorbate Sodium | 1 mM | Potassium Permangante | 5 µM |
| 8 | Ascorbate Sodium | 1 mM | Manganese Gluconate | 5 µM |
| 9 | Reduced Glutathione | 1 mM | Chromium Picolinate | 5 µM |
| 10 | Reduced Glutathione | 1 mM | Copper Chloride | 5 µM |
| 11 | Reduced Glutathione | 1 mM | Vanadium Sulfate | 5 µM |
| 12 | Reduced Glutathione | 1 mM | Vanadium Oxide | 5 µM |
| 13 | Reduced Glutathione | 1 mM | Sodium Vanadate | 5 µM |
| 14 | Reduced Glutathione | 1 mM | Chromium Chloride | 5 µM |
| 15 | Uric Acid | 1 mM | Copper Sulfate | 5 µM |
| 16 | Uric Acid | 1 mM | Sodium Vanadate | 5 µM |
| 17 | Uric Acid | 1 mM | Manganese Gluconate | 5 µM |
| 18 | Uric Acid | 1 mM | Chromium Picolinate | 5 µM |
| 19 | Mannitol | 1 mM | Zinc Sulfate | 5 µM |
| 20 | Mannitol | 1 mM | Vanadium Sulfate | 5 µM |
| 21 | Mannitol | 1 mM | Chromium Picolinate | 5 µM |
| 22 | Benzohydroxamic acid | 1 mM | Copper Sulfate | 5 µM |
| 23 | Benzohydroxamic acid | 1 mM | Vanadium Sulfate | 5 µM |
| 24 | Benzohydroxamic acid | 1 mM | Vanadium Oxide | 5 µM |
| 25 | Benzohydroxamic acid | 1 mM | Sodium Vanadate | 5 µM |
| 26 | Benzohydroxamic acid | 1 mM | Chromium Chloride | 5 µM |
| 27 | Cysteine | 1 mM | Copper Chloride | 5 µM |
| 28 | Cysteine | 1 mM | Vanadium Oxide | 5 µM |
| 29 | Cysteine | 1 mM | Manganese Gluconate | 5 µM |
| 30 | Cysteine | 1 mM | Chromium Picolinate | 5 µM |
| 31 | Piperine | 1 mM | Piperine/None | 5 µM |
| 32 | Inhibitors (control) | 1 mM |  |  |

Determination of Oxidative Inactivation (Activity and pH) of Trypsin in Presence of Combination of Metal Ions and Reducing Agents.

For a 200 µl reaction mixture, about 10 µl trypsin was incubated in buffer with the combination of metal salts and reducing agents (provided in Table 2 at serial number 1 through 31) at respective concentration at 37° C. in 96 well microtitre plates (Table 3 hereinbelow provides details on utilization of a particular combination from those provided at serial number 1 through 31 in Table 2) for 5 min, 15 min and 30 min followed by the addition of respective 90 µl substrate (provided in Table 1A). The enzyme activity was measured spectrophotometrically in a microplate reader, and was compared with original activity assay. The pH was measured by Hanna Combination pH electrode (reaction with enzyme was performed in triplicates). Table 4 below provides enzymatic activity of trypsin after lapse of specific time periods after treatment with the combination of metal salt/complex and reducing agent under evaluation.

TABLE 3

Distribution of combination of metal salt/complex and reducing agent being evaluated in 96 well microtitre plates

| | Con-trol | Control | Control | 1 | 1 | 1 | 2 | 2 | 2 | 3 | 3 | 3 |
|---|---|---|---|---|---|---|---|---|---|---|---|---|
| A | | | | | | | | | | | | |
| B | 4 | 4 | 4 | 5 | 5 | 5 | 6 | 6 | 6 | 7 | 7 | 7 |
| C | 8 | 8 | 8 | 9 | 9 | 9 | 10 | 10 | 10 | 11 | 11 | 11 |
| D | 12 | 12 | 12 | 13 | 13 | 13 | 14 | 14 | 14 | 15 | 15 | 15 |
| E | 16 | 16 | 16 | 17 | 17 | 17 | 18 | 18 | 18 | 19 | 19 | 19 |
| F | 20 | 20 | 20 | 21 | 21 | 21 | 22 | 22 | 22 | 23 | 23 | 23 |
| G | 24 | 24 | 24 | 25 | 25 | 25 | 26 | 26 | 26 | 27 | 27 | 27 |
| H | 28 | 28 | 28 | 29 | 29 | 29 | 30 | 30 | 30 | 31 | 31 | 31 |

TABLE 4

Enzymatic activity of trypsin

| Reducing agents and Metal salts | 5 min | 15 min | 30 min |
|---|---|---|---|
| Ascorbate Sodium:Copper Chloride | 89.65517241 | 66.66666667 | 45.71428571 |
| Ascorbate Sodium:Copper Sulphate | 89.65517241 | 40.25 | 40 |
| Ascorbate Sodium:Zinc Sulphate | 55.17241379 | 54.16666667 | 57.14285714 |
| Ascorbate Sodium:Vanadium Oxide | 41.37931034 | 31.25 | 17.14285714 |
| Ascorbate Sodium:Vanadium Sulphate | 82.75862069 | 20.83333333 | 14.28571429 |
| Ascorbate Sodium:Sodium Vanadate | 27.5862069 | 54.16666667 | 31.42857143 |
| Ascorbate Sodium:Pottasium Permangnate | 165.5172414 | 20.83333333 | 76 |
| Ascorbate Sodium:Manganse Gluconate | 27.5862069 | 29.16666667 | 17.14285714 |
| Reduced Glutathione:Chromium Picolinate | 55.17241379 | 45.83333333 | 71.42857143 |
| Reduced Glutathione:Copper | 158.6206897 | 83.33333333 | 80.57142857 |
| Reduced Glutathione:Vanadium Sulphate | 188.2758621 | 41.66666667 | 37.14285714 |
| Reduced Glutathione:Vanadium Oxide | 20.68965517 | 95.83333333 | 48.57142857 |
| Reduced Glutathione:Sodium Vanadate | 108.0482759 | 58.33333333 | 20 |
| Reduced Glutathione:Chromium | 48.27586207 | 16.91666667 | 5.714285714 |
| Uric Acid:Copper Sulphate | 179.3103448 | 12.5 | 5.714285714 |
| Uric Acid:Sodium Vanadate | 68.96551724 | 29.16666667 | 26.74285714 |
| Uric Acid:Manganese Gluconate | 55.17241379 | 37.5 | 37.14285714 |
| Uric Acid:Chromium Picolinate | 103.4482759 | 33.33333333 | 22.85714286 |
| Mannitol:Zinc Sulfate | 158.6206897 | 70.83333333 | 62.85714286 |
| Mannitol:Vandium Sulphate | 103.4482759 | 95.83333333 | 80 |
| Mannitol:Chromium Picolinate | 89.65517241 | 83.33333333 | 37.14285714 |
| Benzohydroxamic acid:Copper Sulfate | 110.3448276 | 4.166666667 | 57.14285714 |
| Benzohydroxamic acid:Vanadium Sulfate | 43.2137931 | 29.16666667 | 28.57142857 |
| Benzohydroxamic acid:Vanadium Oxide | 158.6206897 | 87.5 | 45.71428571 |
| Benzohydroxamic acid:Sodium Vanadate | 131.0344828 | 66.66666667 | 2.857142857 |
| Benzohydroxamic acid:Chromium Chloride | 68.96551724 | 66.66666667 | 20 |
| Cysteine:Copper Chloride | 117.2413793 | 50 | 40 |
| Cysteine:Vanadium Oxide | 186.2068966 | 16.66666667 | 14.28571429 |
| Cysteine:Manganese Gluconate | 55.17241379 | 58.33333333 | 11.42857143 |
| Cysteine:Chromium Picolinate | 186.2068966 | 25 | 20 |
| Piperine | 172.4137931 | 66.66666667 | 45.71428571 |

Table 5A through 5C provided herein below represents the pH measurement for trypsin at various intervals of times i.e. 5 minutes, 15 minutes and 30 minutes.

TABLE 5A pH measurement for trypsin at an interval of 5 min

| | 1 | 2 | 3 | 4 | 5 | 6 | 7 | 8 | 9 | 10 | 11 | 12 |
|---|---|---|---|---|---|---|---|---|---|---|---|---|
| A | 3.5 | 3.4 | 3.5 | 2.5 | 2.45 | 1.7 | 2.5 | 2.4 | 2.5 | 2.6 | 2.5 | 2.7 |
| B | 2.5 | 2.6 | 2.3 | 2.2 | 2.5 | 2.8 | 2.2 | 2.3 | 2.6 | 2.4 | 2.2 | 2.2 |
| C | 2.5 | 2.2 | 2.5 | 2.5 | 2.5 | 2.5 | 2.5 | 2.5 | 2.8 | 2.5 | 2.5 | 2.5 |
| D | 2.6 | 2.5 | 2.5 | 2.5 | 2.5 | 2.5 | 2.5 | 2.5 | 2.8 | 2.4 | 2.5 | 2.5 |
| E | 2.5 | 2.5 | 2.6 | 2.5 | 2.6 | 2.5 | 2.6 | 2.6 | 2.6 | 2.6 | 2.6 | 2.6 |
| F | 2.6 | 2.6 | 2.6 | 2.6 | 2.6 | 2.6 | 2.6 | 2.6 | 2.6 | 2.6 | 2.6 | 2.6 |
| G | 2.4 | 2.4 | 2.5 | 2.2 | 2.2 | 2.2 | 2.2 | 2.2 | 2.2 | 2 | 2 | 2.8 |
| H | 2.5 | 2.2 | 2.2 | 2 | 2 | 2 | 2 | 2 | 2 | 2.2 | 2.2 | 2.2 |

TABLE 5B pH measurement for trypsin at an interval of 15 min

|   | 1 | 2 | 3 | 4 | 5 | 6 | 7 | 8 | 9 | 10 | 11 | 12 |
|---|---|---|---|---|---|---|---|---|---|----|----|----|
| A | 3.5 | 3.4 | 3.5 | 2.8 | 1.6 | 2.3 | 2.4 | 2.4 | 2.5 | 2.6 | 2.5 | 2.7 |
| B | 2.5 | 2.6 | 2.3 | 2.2 | 2.5 | 2.8 | 2.2 | 2.3 | 2.6 | 2.4 | 2.2 | 2.2 |
| C | 2.5 | 2.2 | 2.5 | 2.5 | 2.5 | 2.5 | 2.5 | 2.5 | 2.8 | 2.5 | 2.5 | 2.5 |
| D | 2.6 | 2.5 | 2.5 | 2.5 | 2.5 | 2.5 | 2.5 | 2.5 | 2.8 | 2.4 | 2.5 | 2.5 |
| E | 2.5 | 2.5 | 2.6 |     | 2.6 | 2.5 | 2.6 | 2.6 | 2.6 | 2.6 | 2.6 | 2.6 |
| F | 2.6 | 2.6 | 2.6 | 2.6 | 2.6 | 2.6 | 2.6 | 2.6 | 2.6 | 2.6 | 2.6 | 2.6 |
| G | 2.4 | 2.4 | 2.5 | 2.2 | 2.2 | 2.2 | 2.2 | 2.2 | 2.2 | 2   | 2  | 2.8 |
| H | 2.5 | 2.2 | 2.2 | 2   | 2   | 2   | 2   | 2   | 2   | 2.2 | 2.2 | 2.2 |

TABLE 5C pH measurement for trypsin at an interval of at 30 min

|   | 1 | 2 | 3 | 4 | 5 | 6 | 7 | 8 | 9 | 10 | 11 | 12 |
|---|---|---|---|---|---|---|---|---|---|----|----|----|
| A | 3.5 | 3.45 | 3.5 | 2.5 | 1.6 | 2.3 | 2.4 | 2.4 | 2.5 | 2.6 | 2.9 | 2.7 |
| B | 2.6 | 2.6 | 2.3 | 2.2 | 2.5 | 2.8 | 2.2 | 2.3 | 2.6 | 2.4 | 2.2 | 2.7 |
| C | 2.7 | 2.2 | 2.5 | 2.1 | 2.5 | 2.5 | 2.5 | 2.5 | 2.8 | 2.5 | 2.5 | 2.5 |
| D | 2.1 | 2.4 | 2.6 | 2.1 | 2.5 | 2.5 | 2.5 | 2.5 | 2.8 | 2.4 | 2.5 | 2.5 |
| E | 2.5 | 2.52 | 2.6 | 2.5 | 2.6 | 2.5 | 2.6 | 2.6 | 2.6 | 2.6 | 2.6 | 2.6 |
| F | 2.6 | 2.6 | 2.6 | 2.6 | 2.6 | 2.6 | 2.6 | 2.6 | 2.6 | 2.6 | 2.6 | 2.6 |
| G | 2.4 | 2.4 | 2.5 | 2.2 | 2.2 | 2.2 | 2.2 | 2.2 | 2.2 | 2   | 2   | 2.8 |
| H | 2.5 | 2.2 | 2.2 | 2   | 2   | 2   | 2   | 2   | 2   | 2.2 | 2.2 | 2.2 |

Assay for Enzymatic Activity of Chymotrypsin Using the Ala-Ala-Phe-7-Amido-4-Methylcoumarin About 2 units of Chymotrypsin cold HCl solution, 1.18 mM substrate solution, 2M calcium chloride solution, 80 mM Tris HCl Buffer solution were prepared separately. In a 3 ml buffer solution, substrate solution and calcium chloride solution were added and mixed by inversion at around 25 degree Celsius to form a blank reaction mixture and a test reaction mixture (Table 6). Further, HCL solution was added in blank reaction mixture and enzyme solution was added in test reaction mixture, mixed immediately by inversion and the increase in absorbance at $A_{256}$ was recorded for 3 to 5 min. The $A_{256}$/min will be obtained for both blank reaction and test reactions using the maximum linear rate over a minute interval using at least 4 data values.

TABLE 6

Scheme for preparation of blank and test solution

| Reagents | Blank (ml) | Test (ml) |
|---|---|---|
| Buffer | 1.42 | 1.42 |
| Substrate Solution | 1.40 | 1.40 |
| CaCl2 Solution | 0.08 | 0.08 |
| Mixed by inversion and temperature will be adjusted to 25° C. | | |
| HCl Solution | 0.10 | — |
| Enzyme Solution | — | 0.10 |

Calculation (for Substrate Ala-Ala-Phe-7-amido-4-methylcoumarin):

$$\text{Units/ml enzyme} = \frac{\Delta A_{256}/\text{minute Test} - \Delta A_{256}/\text{minute Blank}) \times (3) \times (df)}{(83.4) \times (0.10)}$$

wherein, 3=volume (ml) of reaction mix; df=dilution factor; 83.4=millimolar extinction coefficient of substrate at 256 nm; 0.10=volume (ml) of test sample used in assay.

Determination of Inactivation of Chymotrypsin in Presence of Inhibitors:

Chymotrypsin (1 mM/L) was incubated with specific known inhibitors (provide in Table 1A hereinabove), and combination of metal salts and reducing agents (provided in Table 2 hereinabove), separately. Inactivation by inhibitors served as a positive control.

Determination of the Oxidative Inactivation (Activity and pH) of Chymotrypsin in the Presence of Combination of Metal Ions and Reducing Agents.

For a 200 µl reaction mixture, about 10 µl Chymotrypsin was incubated in buffer with the combination of metal salts and reducing agents (provided in Table 2 at serial number 1 through 31) at respective concentration at 37° C. in 96 well microtitre plates (Table 3 hereinabove provides details on utilization of a particular combination from those provided at serial number 1 through 31 in Table 2) for 5 min, 15 min and 30 min followed by the addition of respective 90 µl substrate (provided in Table 1A). The activity was measured spectrophotometrically in a microplate reader, and was compared with original activity assay. The pH was measured by Hanna Combination pH electrode (reaction with enzyme was performed in triplicates). Table 7 below provides enzymatic activity of Chymotrypsin after lapse of specific time periods after treatment with the combination of metal salt/complex and reducing agent under evaluation.

TABLE 7

Enzymatic activity of Chymotrypsin

| Reducing Agent and Metal salts | Time | | |
|---|---|---|---|
| | 5 min | 15 min | 30 min |
| Ascorbate Sodium:Copper Chloride | 36.84210526 | 30 | 25.80645161 |
| Ascorbate Sodium:Copper Sulphate | 168.4210526 | 85 | 106.4516129 |
| Ascorbate Sodium:Zinc Sulphate | 47.36842105 | 55 | 25.80645161 |
| Ascorbate Sodium:Vanadium Oxide | 78.94736842 | 70 | 38.70967742 |
| Ascorbate Sodium:Vanadium Sulphate | 89.47368421 | 65 | 51.61290323 |
| Ascorbate Sodium:Sodium Vanadate | 100 | 95 | 16.12903226 |
| Ascorbate Sodium:Pottasium Permangnate | 163.1578947 | 130 | 9.677419355 |
| Ascorbate Sodium:Manganses Gluconate | 78.94736842 | 70 | 9.677419355 |
| Reduced Glutathione:Chromium Picolinate | 21.05263158 | 30 | 25.80645161 |
| Reduced Glutathione:Copper Chloride | 47.36842105 | 45 | 45.16129032 |
| Reduced Glutathione:Vanadium Sulphate | 115.7894737 | 85 | 25.80645161 |
| Reduced Glutathione:Vanadium Oxide | 105.2631579 | 65 | 45.16129032 |
| Reduced Glutathione:Sodium Vanadate | 105.2631579 | 55 | 16.12903226 |
| Reduced Glutathione:Chromium Chloride | 105.2631579 | 40 | 41.93548387 |
| Uric Acid:Copper Sulphate | 68.42105263 | 20 | 25.80645161 |
| Uric Acid:Sodium Vanadate | 63.15789474 | 20 | 9.677419355 |
| Uric Acid:Manganese Gluconate | 89.47368421 | 85 | 67.74193548 |
| Uric Acid:Chromium Picolinate | 68.42105263 | 65 | 9.677419355 |

TABLE 7-continued

Enzymatic activity of Chymotrypsin

| Reducing Agent and Metal salts | 5 min | 15 min | 30 min |
|---|---|---|---|
| Mannitol:Zinc Sulfate | 100 | 80 | 51.61290323 |
| Mannitol:Vandium Sulphate | 68.42105263 | 35 | 54.83870968 |
| Mannitol:Chromium Picolinate | 115.7894737 | 40 | 19.35483871 |
| Benzohydroxamic acid:Copper Sulfate | 152.6315789 | 80 | 35.48387097 |
| Benzohydroxamic acid:Vanadium Sulfate | 142.1052632 | 110 | 32.25806452 |
| Benzohydroxamic acid:Vanadium Oxide | 100 | 80 | 56.77419355 |
| Benzohydroxamic acid:Sodium Vanadate | 115.7894737 | 45 | 12.90322581 |
| Benzohydroxamic acid:Chromium Chloride | 89.47368421 | 55 | 58.06451613 |
| Cysteine:Copper Chloride | 89.47368421 | 85 | 70.96774194 |
| Cysteine:Vanadium Oxide | 115.7894737 | 140 | 32.25806452 |
| Cysteine:Manganese Gluconate | 63.15789474 | 65 | 29.03225806 |
| Cysteine:Chromium Picolinate | 84.21052632 | 70 | 22.58064516 |
| Piperine | 84.21052632 | 80 | 35.48387097 |

Table 8A through 8C provided below represents the pH measurement for Chymotrypsin at various intervals of times viz. at 5 minutes, 15 minutes and 30 minutes.

TABLE 8A pH measurement for Chymotrypsin at an interval of 5 min

| | 1 | 2 | 3 | 4 | 5 | 6 | 7 | 8 | 9 | 1 | 11 | 12 |
|---|---|---|---|---|---|---|---|---|---|---|---|---|
| A | 1.68 | 1.66 | 1.65 | 1.7 | 1.75 | 1.76 | 1.7 | 1.72 | 1.69 | 1.78 | 1.77 | 1.65 |
| B | 1.65 | 1.77 | 1.7 | 1.76 | 1.75 | 1.78 | 1.75 | 1.7 | 1.67 | 1.7 | 1.69 | 1.7 |
| C | 1.7 | 1.7 | 1.68 | 1.7 | 1.69 | 1.67 | 1.7 | 1.7 | 1.78 | 1.7 | 1.68 | 1.67 |
| D | 1.67 | 1.67 | 1.67 | 1.67 | 1.7 | 1.7 | 1.7 | 1.7 | 1.78 | 1.7 | 1.7 | 1.7 |
| E | 1.67 | 1.67 | 1.67 | 1.67 | 1.7 | 1.7 | 1.7 | 1.7 | 1.67 | 1.7 | 1.7 | 1.7 |
| F | 1.67 | 1.67 | 1.7 | 1.7 | 1.7 | 1.67 | 1.67 | 1.67 | 1.7 | 1.7 | 1.7 | 1.7 |
| G | 1.66 | 1.66 | 1.66 | 1.66 | 1.6 | 1.67 | 1.65 | 1.68 | 1.65 | 1.67 | 1.65 | 1.68 |
| H | 1.65 | 1.67 | 1.67 | 1.65 | 1.67 | 1.68 | 1.68 | 1.69 | 1.69 | 1.67 | 1.65 | 1.63 |

TABLE 8B pH measurement for Chymotrypsin at an interval of 15 min

| | 1 | 2 | 3 | 4 | 5 | 6 | 7 | 8 | 9 | 10 | 11 | 12 |
|---|---|---|---|---|---|---|---|---|---|---|---|---|
| A | 1.68 | 1.66 | 1.65 | 1.68 | 1.65 | 1.68 | 1.7 | 1.77 | 1.65 | 1.75 | 1.65 | 1.65 |
| B | 1.65 | 1.69 | 1.7 | 1.7 | 1.68 | 1.78 | 1.75 | 1.7 | 1.67 | 1.7 | 1.69 | 1.7 |
| C | 1.7 | 1.7 | 1.68 | 1.7 | 1.69 | 1.67 | 1.7 | 1.7 | 1.78 | 1.7 | 1.68 | 1.67 |
| D | 1.67 | 1.67 | 1.67 | 1.67 | 1.7 | 1.7 | 1.7 | 1.68 | 1.69 | 1.7 | 1.7 | 1.7 |
| E | 1.67 | 1.67 | 1.67 | 1.67 | 1.7 | 1.7 | 1.7 | 1.7 | 1.67 | 1.7 | 1.7 | 1.7 |
| F | 1.67 | 1.67 | 1.7 | 1.7 | 1.7 | 1.67 | 1.67 | 1.67 | 1.7 | 1.7 | 1.7 | 1.7 |
| G | 1.66 | 1.66 | 1.66 | 1.66 | 1.6 | 1.67 | 1.65 | 1.68 | 1.69 | 1.67 | 1.65 | 1.68 |
| H | 1.65 | 1.67 | 1.67 | 1.65 | 1.67 | 1.68 | 1.68 | 1.69 | 1.69 | 1.67 | 1.65 | 1.63 |

TABLE 8C pH measurement for Chymotrypsin at an interval of 30 min

| | 1 | 2 | 3 | 4 | 5 | 6 | 7 | 8 | 9 | 10 | 11 | 12 |
|---|---|---|---|---|---|---|---|---|---|---|---|---|
| A | 1.68 | 1.66 | 1.65 | 1.69 | 1.65 | 1.7 | 1.77 | 1.77 | 1.69 | 1.68 | 1..68 | 1.66 |
| B | 1.65 | 1.69 | 1.7 | 1.7 | 1.68 | 1.78 | 1.75 | 1.7 | 1.67 | 1.7 | 1.69 | 1.7 |
| C | 1.7 | 1.7 | 1.68 | 1.7 | 1.69 | 1.67 | 1.7 | 1.7 | 1.78 | 1.7 | 1.68 | 1.67 |
| D | 1.67 | 1.67 | 1.67 | 1.67 | 1.7 | 1.7 | 1.7 | 1.68 | 1.69 | 1.7 | 1.7 | 1.7 |
| E | 1.67 | 1.67 | 1.67 | 1.67 | 1.7 | 1.7 | 1.7 | 1.7 | 1.67 | 1.7 | 1.7 | 1.7 |
| F | 1.67 | 1.67 | 1.7 | 1.7 | 1.7 | 1.67 | 1.67 | 1.67 | 1.7 | 1.7 | 1.7 | 1.7 |
| G | 1.66 | 1.66 | 1.66 | 1.66 | 1.6 | 1.67 | 1.65 | 1.68 | 1.69 | 1.67 | 1.65 | 1.68 |
| H | 1.65 | 1.67 | 1.67 | 1.65 | 1.67 | 1.68 | 1.68 | 1.69 | 1.69 | 1.67 | 1.65 | 1.63 |

Assay for Enzymatic Activity of Carboxypeptidase B Using Hippuryl-Arginine 4 units of Carboxypeptidase B in cold deionized water, 1 mm Hippuryl-Arginine solution in 25 mM Tris Buffer solution containing 100 mM Sodium Chloride (pH 7.65) were prepared, separately at about 25° C. 3 ml reaction mixtures (Test and blank) were prepared using above prepared solutions according to Table 9 at 25° C.

Calculations:

$$\text{Units/ml enzyme} = \frac{(\Delta A_{254\,nm}/\text{min Test} - \Delta A_{254\,nm}/\text{min Blank})(3)(df)}{(0.36)(0.1)}$$

where, 3=volume (ml) of reaction mix; df=dilution factor; 0.36=millimolar extinction coefficient of substrate at 254 nm; 0.10=volume (ml) of test sample used in assay

TABLE 9

Scheme for the preparation of Test and Blank Solution

| Reagents | Test (ml) | Blank (ml) |
|---|---|---|
| (Hippuryl-Arginine solution in Tris Buffer solution containing Sodium Chloride | 2.90 | 2.90 |
| Deionized Water | — | 0.10 |
| Carboxypeptidase B solution | 0.10 | — |

Determination of Inactivation of Carboxypeptidase in Presence of Inhibitors:

Carboxypeptidase (1 mM/L) was incubated with specific known inhibitor (provided in Table 1A hereinabove), and combination of metal salts/Reducing agents (provided in Table 2 hereinabove), separately. Inactivation by inhibitors served as a positive control.

Determination of Oxidative Inactivation (Activity and pH) of Carboxypeptidase in Presence of Combination of Metal Ions and Reducing Agents.

For a 200 μl reaction mixture, about 10 μl Carboxypeptidase was incubated in buffer with the combination of metal salts and reducing agents (provided in Table 2 at serial number 1 through 31) at respective concentration at 37° C. in 96 well microtitre plates (Table 3 hereinabove provides details on utilization of a particular combination from those provided at serial number 1 through 31 in Table 2) for 5 min, 15 min and 30 min followed by the addition of respective 90 μl substrate (provided in Table 1A). The enzyme activity was measured spectrophotometrically in a microplate reader, and was compared with original activity assay. The pH was measured by Hanna Combination pH electrode (reaction with enzyme was performed in triplicates). Table 10 below provides enzymatic activity of Carboxypeptidase after lapse of specific time periods after treatment with the combination of metal salt/complex and reducing agent under evaluation.

TABLE 10

Enzymatic activity of Carboxypeptidase

| Reducing Agent and Metal salts | Time | | |
|---|---|---|---|
| | 5 min | 15 min | 30 min |
| Ascorbate Sodium:Copper Chloride | 43.01886792 | 21.58490566 | 58.11320755 |
| Ascorbate Sodium:Copper Sulphate | 79.24528302 | 87.54716981 | 41.50943396 |
| Ascorbate Sodium:Zinc Sulphate | 120.0113208 | 33.20754717 | 33.20754717 |
| Ascorbate Sodium:Vanadium Oxide | 34.67169811 | 29.05660377 | 0 |
| Ascorbate Sodium:Vanadium Sulphate | 89.13962264 | 66.41509434 | 66.41509434 |
| Ascorbate Sodium:Sodium Vanadate | 61.01886792 | 58.11320755 | 58.49056604 |
| Ascorbate Sodium:Pottasium Permangnate | 83.39622642 | 58.11320755 | 41.50943396 |
| Ascorbate Sodium:Manganses Gluconate | 49.81132075 | 62.26415094 | 66.41509434 |
| Reduced Glutathione:Chromium Picolinate | 65.09433962 | 29.05660377 | 20.75471698 |
| Reduced Glutathione:Copper Chloride | 100 | 58.11320755 | 75.09433962 |
| Reduced Glutathione:Vanadium Sulphate | 91.69811321 | 33.20754717 | 0 |
| Reduced Glutathione:Vanadium Oxide | 79.24528302 | 45.66037736 | 20.75471698 |
| Reduced Glutathione:Sodium Vanadate | 49.43396226 | 41.50943396 | 37.35849057 |
| Reduced Glutathione:Chromium Chloride | 79.24528302 | 4.150943396 | 58.49056604 |
| Uric Acid:Copper Sulphate | 100 | 62.26415094 | 49.81132075 |
| Uric Acid:Sodium Vanadate | 83.77358491 | 53.96226415 | 29.05660377 |
| Uric Acid:Manganese Gluconate | 95.8490566 | 45.66037736 | 45.66037736 |
| Uric Acid:Chromium Picolinate | 62.26415094 | 50.18867925 | 45.66037736 |
| Mannitol:Zinc Sulfate | 74.71698113 | 62.26415094 | 41.50943396 |
| Mannitol:Vandium Sulphate | 56.22641509 | 37.35849057 | 37.35849057 |
| Mannitol:Chromium Picolinate | 79.24528302 | 58.11320755 | 58.11320755 |

TABLE 10-continued

Enzymatic activity of Carboxypeptidase

| Reducing Agent and Metal salts | Time | | |
|---|---|---|---|
| | 5 min | 15 min | 30 min |
| Benzohydroxamic acid:Copper Sulfate | 91.32075472 | | 83.39622642 |
| Benzohydroxamic acid:Vanadium Sulfate | 45.66037736 | 24.90566038 | 16.60377358 |
| Benzohydroxamic acid:Vanadium Oxide | 79.24528302 | 79.24528302 | 49.81132075 |
| Benzohydroxamic acid:Sodium Vanadate | 41.50943396 | 33.20754717 | 24.90566038 |
| Benzohydroxamic acid: Chromium Chloride | 54.33962264 | 24.90566038 | 12.45283019 |
| Cysteine:Copper Chloride | 87.54716981 | 41.50943396 | 16.60377358 |
| Cysteine:Vanadium Oxide | 33.20754717 | 25.94339623 | 25.94339623 |
| Cysteine:Manganese Gluconate | 49.81132075 | 74.71698113 | 62.26415094 |
| Cysteine:Chromium Picolinate | 70.94339623 | 41.50943396 | 6.918238994 |
| Piperine | 104.5283019 | 91.69811321 | 62.26415094 |

Table 11A through 11C represents the pH measurement for Carboxypeptidase at various intervals of times viz. at 5 minutes, 15 minutes and 30 minutes.

TABLE 11A pH measurement for Carboxypeptidase at an interval of 5 min

| | 1 | 2 | 3 | 4 | 5 | 6 | 7 | 8 | 9 | 10 | 11 | 12 |
|---|---|---|---|---|---|---|---|---|---|---|---|---|
| A | 7.77 | 7.78 | 7.76 | 7.76 | 7.65 | 7.77 | 7.77 | 7.78 | 7.76 | 7.65 | 7.78 | 7.7 |
| B | 7.78 | 7.8 | 7.67 | 7.78 | 7.79 | 7.69 | 7.72 | 7.67 | 7.74 | 7.75 | 7.76 | 7.78 |
| C | 7.79 | 7.76 | 7.75 | 7.76 | 7.78 | 7.7 | 7.6 | 7.8 | 7.7 | 7.5 | 7.67 | 7.7 |
| D | 7.8 | 7.76 | 7.7 | 7.6 | 7.72 | 7.6 | 7.9 | 7.7 | 7.7 | 7.7 | 7.8 | 7.8 |
| E | 7.76 | 7.6 | 7.78 | 7.7 | 7.6 | 7.6 | 7.8 | 7.6 | 7.7 | 7.76 | 7.8 | 7.7 |
| F | 7.7 | 7.8 | 7.7 | 7.7 | 7.7 | 7.8 | 7.8 | 7.7 | 7.7 | 7.7 | 7.7 | 7.7 |
| G | 7.7 | 7.8 | 7.71 | 7.75 | 7.8 | 7.8 | 7.7 | 7.78 | 7.7 | 7.7 | 7.7 | 7.7 |
| H | 7.67 | 7.6 | 7.6 | 7.76 | 7.8 | 7.7 | 7.7 | 7.7 | 7.7 | 7.7 | 7.7 | 7.7 |

TABLE 11B pH measurement for Carboxypeptidase at an interval of 15 min

| | 1 | 2 | 3 | 4 | 5 | 6 | 7 | 8 | 9 | 10 | 11 | 12 |
|---|---|---|---|---|---|---|---|---|---|---|---|---|
| A | 7.77 | 7.7 | 7.7 | 7.7 | 7.75 | 7.77 | 7.77 | 7.78 | 7.76 | 7.65 | 7.78 | 7.7 |
| B | 7.78 | 7.8 | 7.67 | 7.78 | 7.79 | 7.69 | 7.72 | 7.67 | 7.74 | 7.75 | 7.76 | 7.78 |
| C | 7.79 | 7.76 | 7.75 | 7.76 | 7.78 | 7.7 | 7.6 | 7.8 | 7.7 | 7.5 | 7.67 | 7.7 |
| D | 7.8 | 7.76 | 7.7 | 7.6 | 7.72 | 7.6 | 7.9 | 7.7 | 7.7 | 7.7 | 7.7 | 7.7 |
| E | 7.76 | 7.6 | 7.78 | 7.7 | 7.6 | 7.6 | 7.8 | 7.6 | 7.7 | 7.76 | 7.8 | 7.7 |
| F | 7.7 | 7.8 | 7.7 | 7.7 | 7.7 | 7.8 | 7.8 | 7.7 | 7.7 | 7.7 | 7.7 | 7.7 |
| G | 7.7 | 7.8 | 7.71 | 7.75 | 7.8 | 7.8 | 7.7 | 7.78 | 7.7 | 7.7 | 7.7 | 7.7 |
| H | 7.67 | 7.6 | 7.6 | 7.76 | 7.8 | 7.7 | 7.7 | 7.7 | 7.7 | 7.7 | 7.7 | 7.7 |

TABLE 11C pH measurement for Carboxypeptidase at an interval of 30 min

| | 1 | 2 | 3 | 4 | 5 | 6 | 7 | 8 | 9 | 10 | 11 | 12 |
|---|---|---|---|---|---|---|---|---|---|---|---|---|
| A | 7.77 | 7.7 | 7.7 | 7.8 | 7.75 | 7.77 | 7.77 | 7.78 | 7.76 | 7.65 | 7.78 | 7.7 |
| B | 7.78 | 7.9 | 7.67 | 7.78 | 7.79 | 7.69 | 7.72 | 7.67 | 7.74 | 7.75 | 7.76 | 7.78 |
| C | 7.79 | 7.8 | 7.75 | 7.76 | 7.78 | 7.7 | 7.6 | 7.8 | 7.7 | 7.5 | 7.67 | 7.7 |
| D | 7.8 | 7.76 | 7.7 | 7.6 | 7.72 | 7.6 | 7.9 | 7.7 | 7.7 | 7.7 | 7.8 | 7.6 |
| E | 7.76 | 7.6 | 7.78 | 7.7 | 7.6 | 7.6 | 7.8 | 7.6 | 7.7 | 7.76 | 7.8 | 7.7 |

TABLE 11C-continued pH measurement for Carboxypeptidase at an interval of 30 min

|   | 1    | 2   | 3    | 4    | 5   | 6   | 7   | 8    | 9   | 10  | 11  | 12  |
|---|------|-----|------|------|-----|-----|-----|------|-----|-----|-----|-----|
| F | 7.7  | 7.8 | 7.7  | 7.7  | 7.7 | 7.8 | 7.8 | 7.7  | 7.7 | 7.7 | 7.7 | 7.7 |
| G | 7.7  | 7.8 | 7.71 | 7.75 | 7.8 | 7.8 | 7.7 | 7.78 | 7.7 | 7.7 | 7.7 | 7.7 |
| H | 7.67 | 7.6 | 7.6  | 7.76 | 7.8 | 7.7 | 7.7 | 7.7  | 7.7 | 7.7 | 7.7 | 7.7 |

To Assay the Enzymatic Activity of Aminopeptidase M Using L-Leucine-p-Nitroanilide 1 mM Tricine solution (Prepared in 100 ml deionized water, Reagent A) and 50 mM L-Leucine-p-nitroanilide solution in absolute methanol (Reagent B) were prepared, separately. About 10 mM L-Leucine-p-nitroanilide solution (Leu-Na, Reagent C) was prepared by adding 0.1 ml of Reagent B into 4.9 ml of Reagent A. 200 mM Tricine Buffer in deionized water (Reagent D) and 200 mM Tricine Buffer with 0.05% (w/v) BSA pH 8.0 at 25° C. (Reagent E) were prepared, separately. 0.04 units/ml Aminopeptidase was prepared in Reagent E (Enzyme solution, Reagent F). Reagent C, (Leu-NA, 2.0 ml), Reagent D (200 mM Tricine Buffer, 1.0 ml) and deionised water (7.0 ml) were pipetted and mixed in a container by swirling to give a reaction cocktail (Reagent G). Reagent G, Reagent E and Reagent F were mixed immediately by inversion to prepare test and blank solution as directed in table 12, and the increase in $\Delta A_{405}$ nm was recorded for approximately 5 minutes. $\Delta A405$ nm/minute was obtained using maximum linear rate for both the Test and blank solution.

Calculations:

$$\text{Units/ml enzyme} = \frac{(\Delta A_{405\,nm}/\text{min Test} - \Delta A_{405\,nm}/\text{min Blank})(1)(df)}{(0.36)(0.1)}$$

where, 1=Total volume (ml) of assay; df=Dilution factor; 10.8=Millimolar extinction coefficient 1 of p-Nitroaniline at A405 nm; 0.1=Volume (in milliliter) of enzyme used.

TABLE 12

Scheme for the preparation of Test and Blank solution

| Reagents | Test (ml) | Blank (ml) |
|---|---|---|
| Reaction cocktail (Reagent G) | 0.90 | 0.90 |
| Reagent F (Enzyme Solution) | 0.10 | — |
| Reagent E | — | 0.10 |

Determination of Inactivation of Aminopeptidase in Presence of Inhibitors:

Aminopeptidase (1 mM/L) was incubated with specific inhibitor (provide in Table 1A hereinabove), and combination of metal salts/Reducing agents (provided in Table 2 hereinabove), separately. Inactivation by inhibitors served as a positive control.

Determination of Oxidative Inactivation (Activity and pH) of Aminopeptidase in Presence of Combination of Metal Ions and Reducing Agents.

For a 200 µl reaction mixture, about 10 µl Aminopeptidase was incubated in buffer with the combination of metal salts and reducing agents (provided in Table 2 at serial number 1 through 31) at respective concentration at 37° C. in 96 well microtitre plates (Table 3 hereinabove provides details on utilization of a particular combination from those provided at serial number 1 through 31 in Table 2) for 5 min, 15 min and 30 min followed by the addition of respective 90 µl substrate (provided in Table 1A). The enzyme activity was measured spectrophotometrically in a microplate reader, and was compared with original activity assay. The pH was measured by Hanna Combination pH electrode (reaction with enzyme was performed in triplicates). Table 13 below provides enzymatic activity of Aminopeptidase after lapse of specific time periods after treatment with the combination of metal salt/complex and reducing agent under evaluation.

TABLE 13

Enzymatic activity of Aminopeptidase

| Reducing Agent and Metal salts | Time | | |
|---|---|---|---|
| | 5 min | 15 min | 30 min |
| Ascorbate Sodium:Copper Chloride | 100 | 98.06034483 | 91.31455399 |
| Ascorbate Sodium:Copper Sulphate | 92.57142857 | 81.89655172 | 91.07981221 |
| Ascorbate Sodium:Zinc Sulphate | 109.1428571 | 105.1724138 | 101.6431925 |
| Ascorbate Sodium:Vanadium Oxide | 113.4285714 | 109.9137931 | 80.51643192 |
| Ascorbate Sodium:Vanadium Sulphate | 99.42857143 | 99.13793103 | 99.06103286 |
| Ascorbate Sodium:Sodium Vanadate | 101.7142857 | 90.94827586 | 73.94366197 |

TABLE 13-continued

Enzymatic activity of Aminopeptidase

| Reducing Agent and Metal salts | 5 min | 15 min | 30 min |
|---|---|---|---|
| Ascorbate Sodium:Pottasium Permangnate | 100 | 99.56896552 | 88.2629108 |
| Ascorbate Sodium:Manganses Gluconate | 104.8571429 | 100.4310345 | 100.4694836 |
| Reduced Glutathione:Chromium Picolinate | 92.57142857 | 87.5 | 79.10798122 |
| Reduced Glutathione:Copper Chloride | 96 | 94.39655172 | 88.96713615 |
| Reduced Glutathione:Vanadium Sulphate | 96 | 86.42241379 | 83.09859155 |
| Reduced Glutathione:Vanadium Oxide | 102 | 98.27586207 | 100.4694836 |
| Reduced Glutathione:Sodium Vanadate | 96 | 95.04310345 | 84.50704225 |
| Reduced Glutathione:Chromium Chloride | 108.2857143 | 95.68965517 | 89.20187793 |
| Uric Acid:Copper Sulphate | 94.51428571 | 93.53448276 | 97.18309859 |
| Uric Acid:Sodium Vanadate | 102.8571429 | 101.7241379 | 99.29577465 |
| Uric Acid:Manganese Gluconate | 98.57142857 | 95.68965517 | 93.42723005 |
| Uric Acid:Chromium Picolinate | 93.42857143 | 93.53448276 | 86.61971831 |
| Mannitol:Zinc Sulfate | 105.1428571 | 90.0862069 | 96.24413146 |
| Mannitol:Vandium Sulphate | 106.5714286 | 101.7241379 | 99.06103286 |
| Mannitol:Chromium Picolinate | 94 | 87.71551724 | 101.8779343 |
| Benzohydroxamic acid:Copper Sulfate | 89.71428571 | 75.86206897 | 74.64788732 |
| Benzohydroxamic acid:Vanadium Sulfate | 84 | 70.68965517 | 75.11737089 |
| Benzohydroxamic acid:Vanadium Oxide | 87.42857143 | 85.12931034 | 77.9342723 |
| Benzohydroxamic acid:Sodium Vanadate | 64.51428571 | 88.36206897 | 79.81220657 |
| Benzohydroxamic acid:Chromium Chloride | 96.85714286 | 67.88793103 | 78.16901408 |
| Cysteine:Copper Chloride | 110 | 113.362069 | 114.5539906 |
| Cysteine:Vanadium Oxide | 93.71428571 | 88.57758621 | 88.2629108 |
| Cysteine:Manganese Gluconate | 88 | 88.36206897 | 88.73239437 |
| Cysteine:Chromium Picolinate | 105.4285714 | 90.94827586 | 64.31924883 |
| Piperine | 108 | 100.4310345 | 80.51643192 |

Table 14A through 14C provided herein below represents the pH measurement for Aminopeptidase at various intervals of times viz. at 5 minutes, 15 minutes and 30 minutes.

TABLE 14A pH measurement for Aminopeptidase at an interval of 5 min

|   | 1 | 2 | 3 | 4 | 5 | 6 | 7 | 8 | 9 | 10 | 11 | 12 |
|---|---|---|---|---|---|---|---|---|---|---|---|---|
| A | 8.11 | 8.15 | 8.16 | 8.16 | 8.13 | 8.13 | 8.11 | 8.13 | 8.13 | 8.13 | 8.11 | 8.13 |
| B | 8.13 | 8.1 | 8.11 | 8.12 | 8.09 | 8.09 | 8.1 | 8.1 | 8.09 | 8.11 | 8.1 | 8.12 |
| C | 8.11 | 8.12 | 8.09 | 8.1 | 8.11 | 8.12 | 8.09 | 8.11 | 8.11 | 8.12 | 8.09 | 8.11 |
| D | 8.11 | 8.11 | 8.12 | 8.12 | 8.11 | 8.11 | 8.1 | 8.11 | 8.1 | 8.12 | 8.12 | 8.12 |
| E | 8.11 | 8.11 | 8.12 | 8.1 | 8.11 | 8.11 | 8.12 | 8.11 | 8.09 | 8.11 | 8.1 | 8.11 |
| F | 8.12 | 8.12 | 8.12 | 8.11 | 8.12 | 8.09 | 8.11 | 8.1 | 8.1 | 8.1 | 8.1 | 8.1 |
| G | 8.11 | 8.11 | 8.12 | 8.11 | 8.11 | 8.1 | 8.11 | 8.11 | 8.12 | 8.1 | 8.1 | 8.1 |
| H | 8.1 | 8.1 | 8.1 | 8.1 | 8.12 | 8.12 | 8.1 | 8.1 | 8.12 | 8.12 | 8.12 | 8.12 |

TABLE 14B pH measurement for Aminopeptidase at an interval of 15 min

|   | 1 | 2 | 3 | 4 | 5 | 6 | 7 | 8 | 9 | 10 | 11 | 12 |
|---|---|---|---|---|---|---|---|---|---|---|---|---|
| A | 8.11 | 8.15 | 8.16 | 8.16 | 8.13 | 8.13 | 8.11 | 8.13 | 8.13 | 8.13 | 8.11 | 8.13 |
| B | 8.13 | 8.1 | 8.11 | 8.12 | 8.13 | 8.14 | 8.1 | 8.1 | 8.11 | 8.11 | 8.1 | 8.12 |
| C | 8.11 | 8.12 | 8.12 | 8.1 | 8.11 | 8.12 | 8.13 | 8.11 | 8.11 | 8.12 | 8.15 | 8.11 |

TABLE 14B-continued pH measurement for Aminopeptidase at an interval of 15 min

|   | 1 | 2 | 3 | 4 | 5 | 6 | 7 | 8 | 9 | 10 | 11 | 12 |
|---|---|---|---|---|---|---|---|---|---|----|----|----|
| D | 8.11 | 8.11 | 8.12 | 8.12 | 8.11 | 8.11 | 8.1 | 8.11 | 8.1 | 8.12 | 8.12 | 8.12 |
| E | 8.11 | 8.11 | 8.12 | 8.1 | 8.11 | 8.11 | 8.12 | 8.11 | 8.14 | 8.11 | 8.1 | 8.11 |
| F | 8.12 | 8.12 | 8.12 | 8.11 | 8.12 | 8.14 | 8.11 | 8.1 | 8.1 | 8.1 | 8.1 | 8.1 |
| G | 8.11 | 8.11 | 8.12 | 8.11 | 8.11 | 8.1 | 8.11 | 8.11 | 8.12 | 8.1 | 8.1 | 8.1 |
| H | 8.1 | 8.1 | 8.1 | 8.1 | 8.12 | 8.12 | 8.1 | 8.1 | 8.12 | 8.12 | 8.12 | 8.12 |

TABLE 14C pH measurement for Aminopeptidase at an interval of 30 min

|   | 1 | 2 | 3 | 4 | 5 | 6 | 7 | 8 | 9 | 10 | 11 | 12 |
|---|---|---|---|---|---|---|---|---|---|----|----|----|
| A | 8.11 | 8.15 | 8.16 | 8.16 | 8.13 | 8.13 | 8.11 | 8.13 | 8.13 | 8.13 | 8.11 | 8.13 |
| B | 8.13 | 8.1 | 8.11 | 8.12 | 8.15 | 8..12 | 8.1 | 8.1 | 8.09 | 8.11 | 8.1 | 8.12 |
| C | 8.11 | 8.12 | 8.15 | 8.1 | 8.11 | 8.12 | 8.09 | 8.11 | 8.11 | 8.12 | 8.09 | 8.11 |
| D | 8.11 | 8.11 | 8.12 | 8.12 | 8.11 | 8.11 | 8.1 | 8.11 | 8.1 | 8.12 | 8.12 | 8.12 |
| E | 8.11 | 8.11 | 8.12 | 8.1 | 8.11 | 8.11 | 8.12 | 8.11 | 8.09 | 8.11 | 8.1 | 8.11 |
| F | 8.12 | 8.12 | 8.12 | 8.11 | 8.12 | 8.09 | 8.11 | 8.1 | 8.1 | 8.1 | 8.1 | 8.1 |
| G | 8.11 | 8.11 | 8.12 | 8.11 | 8.11 | 8.1 | 8.11 | 8.11 | 8.12 | 8.1 | 8.1 | 8.1 |
| H | 8.1 | 8.1 | 8.1 | 8.1 | 8.12 | 8.12 | 8.1 | 8.1 | 8.12 | 8.12 | 8.12 | 8.12 |

Based on the experiments carried out and as provided hereinabove, it could be concluded that highest level of inhibition of enzyme activity (proteolytic degradation) was observed by utilization of following combinations of reducing agents and metal salts: Ascorbate Sodium-Vanadium Oxide; Benzohydroxamic acid-Vanadium Sulfate; Mannitol-Vandium Sulphate; Uric Acid-Manganese Gluconate; Reduced Glutathione-Chromium Chloride and Reduced Glutathione-Vanadium Oxide.

Bioavailability Studies

To afford protection from acidic pH of gastric environment and degradation by proteolytic enzymes, capsule-in-capsule formulations were prepared, wherein enteric coated capsule can protect the peptide from gastric environment, MIRA granules present in the outer capsule can inactivate the proteolytic enzymes and permeation enhancers can fasten/increase the absorption of peptide through intestinal epithelial membrane.

Preparation of Capsule-in-Capsule Formulations

Preparation of Granules Containing Reducing Agent(s) and Metal Salt(s)

Table 15A through 15F below presents various reducing agent(s) and metal salt(s) containing granule formulations (referred to herein as MIRA granules), prepared for evaluation of bioavailabilities.

TABLE 15A

Formula for MIRA 1 granules (Rat studies)

| Sr. No | Ingredients | Quantity per capsule |
|--------|-------------|----------------------|
| 1 | Reduced glutathione | 12 mg |
| 2 | Chromium picolinate | 0.03 mg |
| 3 | Microcrystalline Cellulose 101 | 12 mg |
| 4 | Croscarmellose Sodium | 1.5 mg |
| 5 | Mannitol | 4.47 mg |
| 6 | HPMC-E-5 | Q.S. |
| Total | | 30 mg |

TABLE 15B

Formula for MIRA 2 granules (Rat studies)

| Sr. No | Ingredients | Quantity per capsule |
|--------|-------------|----------------------|
| 1 | Ascorbate Sodium | 30 mg |
| 2 | Vanadium oxide | 0.03 mg |
| 3 | Microcrystalline Cellulose 101 | 12 mg |
| 4 | Mannitol | 5.47 mg |
| 5 | Croscarmellose Sodium | 2.5 mg |
| 6 | HPMC-E-5 | Q.S. |
| Total | | 50 mg |

TABLE 15C

Formula for MIRA 3 granules (Rat studies)

| Sr. No | Ingredients | Quantity per capsule |
|--------|-------------|----------------------|
| 1 | Uric acid | 3 mg |
| 2 | Sodium vanadate | 0.03 mg |
| 3 | Microcrystalline Cellulose 101 | 12 mg |

TABLE 15C-continued

Formula for MIRA 3 granules (Rat studies)

| Sr. No | Ingredients | Quantity per capsule |
|---|---|---|
| 4 | Mannitol | 3.97 mg |
| 5 | Croscarmellose Sodium | 1 mg |
| 6 | HPMC-E-5 | Q.S. |
| | Total | 20 mg |

TABLE 15D

Formula for MIRA 4 granules (Rat studies)

| Sr. No | Ingredients | Quantity per capsule |
|---|---|---|
| 1 | Ascorbate Sodium | 30 mg |
| 2 | Manganese gluconate | 0.03 mg |
| 3 | Microcrystalline Cellulose 101 | 12 mg |
| 4 | Mannitol | 5.47 mg |
| 5 | Croscarmellose Sodium | 1.5 mg |
| 6 | HPMC-E-5 | Q.S. |
| | Total | 50 mg |

TABLE 15E

Formula for MIRA 5 granules (Dog studies)

| Sr. No | Ingredients | Quantity per capsule |
|---|---|---|
| 1 | Ascorbate Sodium | 100 mg |
| 2 | Vanadium sulfate | 0.1 mg |
| 3 | Microcrystalline Cellulose 101 | 50 mg |
| 4 | Croscarmellose Sodium | 10 mg |
| 5 | HPMC-E-5 | Q.S. |
| | Total | 160.1 mg |

TABLE 15F

Formula for MIRA 2 granules (Dog studies)

| Sr. No | Ingredients | Quantity per capsule |
|---|---|---|
| 1 | Ascorbate Sodium | 100 mg |
| 2 | Vanadium oxide | 0.1 mg |
| 3 | Microcrystalline Cellulose 101 | 50 mg |
| 4 | Croscarmellose Sodium | 10 mg |
| 5 | HPMC-E-5 | Q.S. |
| | Total | 160.1 mg |

Preparation of MIRA Granules:
MIRA granules were prepared as per below mentioned procedure.

A) Preparation of Binder solution: 0.3% W/V of HPMC E-5 solution was prepared by dissolving 75.0 mg of HPMC E-5 in 25.0 mL of De-ionized (D.I.) water. B) Preparation of Powder blend: All the ingredients were added one by one to a suitable vessel and then mixed thoroughly using a polybag to ensure uniformity of blend. C) Preparation of Granules: Hand granulation was employed to formulate granules by dropwise addition of 2.0 mL of binder solution. (2 ml required to granulate for 2.5 gm powder blend) D) Drying of Granules: Granules prepared were dried at 40° C. for about 12 hours in hot air oven. E) Sifting of Granules: Dried granules were passed through a stainless steel 40# mesh, collected in a suitable glass container and stored at room temperature. (Temperature: 23° C. and Humidity: 39% RH was noted throughout the granulation procedure)

Preparation of Granules Containing Peptide(s)

Table 16A through 16I below presents various peptide(s) containing granule formulations (referred to herein as PA granules), prepared for evaluation of bioavailabilities.

TABLE 16A

Formula for insulin glargine granules PA 1 (Rat studies)

| Sr. No | Ingredients | Quantity per capsule |
|---|---|---|
| 1 | Chenodeoxycholic acid | 30 mg |
| 2 | Insulin glargine | 0.06 mg |
| 3 | Microcrystalline Cellulose 101 | 15 mg |
| 4 | Mannitol | 2.44 mg |
| 5 | Croscarmellose Sodium | 2.5 mg |
| 6 | HPMC-E-5 | Q.S. |
| | Total | 50 mg |

TABLE 16B

Formula for insulin glargine granules PA 2 (Rat studies)

| Sr. No | Ingredients | Quantity per capsule |
|---|---|---|
| 1 | Labrasol ALF | 5 mg |
| 2 | Insulin glargine | 0.06 mg |
| 3 | Microcrystalline Cellulose 101 | 35 mg |
| 4 | Mannitol | 7.44 mg |
| 5 | Croscarmellose Sodium | 2.5 mg |
| 6 | HPMC-E-5 | Q.S. |
| | Total | 50 mg |

TABLE 16C

Formula for octreotide acetate granules PA 1 (Rat studies)

| Sr. No | Ingredients | Quantity per capsule |
|---|---|---|
| 1 | Chenodeoxycholic acid | 30 mg |
| 2 | Octreotide acetate | 0.3 mg |
| 3 | Microcrystalline Cellulose 101 | 15 mg |
| 4 | Mannitol | 2.2 mg |
| 5 | Croscarmellose Sodium | 2.5 mg |
| 6 | HPMC-E-5 | Q.S. |
| | Total | 50 mg |

TABLE 16D

Formula for teriparatide granules PA 1 (Rat studies)

| Sr. No | Ingredients | Quantity per capsule |
|---|---|---|
| 1 | Chenodeoxycholic acid | 30 mg |
| 2 | Teriparatide | 0.12 mg |
| 3 | Microcrystalline Cellulose 101 | 15 mg |
| 4 | Mannitol | 2.38 mg |
| 5 | Croscarmellose Sodium | 2.5 mg |
| 6 | HPMC-E-5 | Q.S. |
| Total | | 50 mg |

TABLE 16E

Formula for teriparatide granules PA 3 (Rat studies)

| Sr. No | Ingredients | Quantity per capsule |
|---|---|---|
| 1 | Piperine | 3 mg |
| 2 | Teriparatide | 0.12 mg |
| 3 | Microcrystalline Cellulose 101 | 20 mg |
| 4 | Mannitol | 5.38 mg |
| 5 | Croscarmellose Sodium | 1.5 mg |
| 6 | HPMC-E-5 | Q.S. |
| Total | | 30 mg |

TABLE 16F

Formula for Liraglutide sodium granules PA 2 (Dog studies)

| Sr. No | Ingredients | Quantity per capsule |
|---|---|---|
| 1 | Liraglutide sodium | 12 mg |
| 2 | Labrasol ALF | 40 mg |
| 3 | Microcrystalline Cellulose 101 | 100 mg |
| 4 | Croscarmellose Sodium | 10 mg |
| 5 | HPMC-E-5 | Q.S. |
| Total | | 162 mg |

TABLE 16G

Formula for Liraglutide sodium granules PA 3 + 4 (Dog studies)

| Sr. No | Ingredients | Quantity per capsule |
|---|---|---|
| 1 | Liraglutide sodium | 12 mg |
| 2 | Piperine | 10 mg |
| 3 | Solutol HS 15 | 25 mg |
| 4 | Microcrystalline Cellulose 101 | 100 mg |
| 5 | Croscarmellose Sodium | 10 mg |
| 6 | HPMC-E-5 | Q.S. |
| Total | | 157 mg |

TABLE 16H

Formula for leuprolide acetate granules PA 2 (Dog studies)

| Sr. No | Ingredients | Quantity per capsule |
|---|---|---|
| 1 | leuprolide acetate | 1.25 mg |
| 2 | Labrasol ALF | 40 mg |
| 3 | Microcrystalline Cellulose 101 | 88.75 mg |
| 4 | Croscarmellose Sodium | 10 mg |
| 5 | HPMC-E-5 | Q.S. |
| Total | | 140 mg |

TABLE 16I

Formula for leuprolide acetate granules PA 2 + 3 (Dog studies)

| Sr. No | Ingredients | Quantity per capsule |
|---|---|---|
| 1 | leuprolide acetate | 1.25 mg |
| 2 | Labrasol ALF | 30 mg |
| 3 | Piperine | 10 mg |
| 4 | Microcrystalline Cellulose 101 | 88.75 mg |
| 5 | Croscarmellose Sodium | 10 mg |
| 6 | HPMC-E-5 | Q.S. |
| Total | | 140 mg |

Granulation Procedure for Peptide Granules

A. Preparation of Binder solution: 0.3% W/V of HPMC E-5 solution was prepared by dissolving 75.0 mg of HPMC E-5 in 25.0 mL of De-ionized (D.I.) water. B. Preparation of Powder blend: All the ingredients except Liquid excipients were weighed accurately and mixed in polybag for 5.0 minutes. C. Addition of Binder: Weighed quantity of Liquid excipients along with peptide was added in HPMC E-5 (0.03%) binder solution. Resulting mixture was added dropwise to perform wet granulation. D. Drying of Granules: Granules were dried in a vacuum desiccator over silica bed overnight. E. Sifting of Granules: Dried granules were passed through a stainless steel 40# mesh, collected in a suitable glass container and stored at room temperature. (Temperature: 22° C. and Humidity: 35% RH was noted throughout the granulation procedure)

Capsule Filling

MIRA and peptide granules were filled in capsules manually using weighing balance Table 17A and 17B below provides size of capsules used for capsules filling for rat studies and dog studies, respectively.

TABLE 17A

Capsule size used for capsules filling for rat studies

| Sr. no | Granules | Size |
|---|---|---|
| 1 | Insulin glargine + Chenodeoxycholic acid | 3 |
| 2 | Insulin glargine + Labrasol | 3 |
| 3 | Octreotide acetate + Chenodeoxycholic acid | 3 |
| 4 | Reduced glutathione + Chromium picolinate | 1 |
| 5 | Ascorbate sodium + Vanadium oxide | 0 |

TABLE 17A-continued

Capsule size used for capsules filling for rat studies

| Sr. no | Granules | Size |
|---|---|---|
| 6 | Uric acid + Sodium vanadate | 4 |
| 7 | Teriparatide + Piperine | 3 |
| 8 | Teriparatide + Chenodeoxycholic acid | 3 |
| 9 | Ascorbate sodium + Manganese gluconate | 0 |

TABLE 17B

Capsule size used for capsules filling for dog studies

| Sr. no | Granules | Size |
|---|---|---|
| 1 | Ascorbate sodium + Vanadium sulfate | 00 (Enteric) |
| 2 | Ascorbate sodium + Vanadium oxide | 00 (Enteric) |
| 3 | Liraglutide sodium + Solutol + Piperine | 3 |
| 4 | Liraglutide sodium + Labrasol | 3 |
| 5 | Leuprolide acetate + Labrasol | 3 |
| 6 | Leuprolide acetate + Labrasol + Piperine | 3 |

Packaging and Storage of Capsules

Capsules were packed in polybags and transferred to HDPE (High density polyethylene) containers with silica bags for moisture control.

Preparation of Placebo Granule Batches

Placebo batch was prepared using sunset yellow and blue colour in order to understand disintegration and release of granules from capsules (visually). Dried granules were filled in size 3 capsules and disintegration time was determined on disintegration tester (Electrolab) using guided discs. Disintegration time was found to be 3±1 min in water and in phosphate buffer (pH 6.8) at 37±0.2° C.

Release Study of Placebo Granules (Capsule in Capsule)

Outer capsule: size 0: yellow coloured granules

Inner capsule: Size 4: Blue coloured granules

Release study was carried out in disintegration apparatus (Electrolab Mumbai) at 37±0.5P in 900 mL of 0.1N HCl (For 2 hr) and pH 6.8 Phosphate buffer.

It could be concluded from visual observation that outer enteric coated capsules remain intact in 0.1 N HCl (Stable in gastric media) whereas started disintegrating in pH 6.8 Phosphate buffer within 3 minutes.

Inner capsules started disintegrating at 8 min and dissolved completely within 13 minutes. In similar way release of MIRA granules can occur at 3 min after when exposed to alkaline PH followed by completes release of peptide within 13 minutes.

Evaluation of Capsules

Assay Procedure Insulin Glargine, Octreotide Acetate and Teriparatide for Rat Studies—

50 mg/30 mg of Granules (removed form one capsule) was weighed accurately and dissolved in mobile phase. Dispersion was sonicated for 5 min in bath sonicator and filtered through 0.22 μm syringe filter and injected in HPLC. Calibration curve for all API were plotted using multiple dilutions in their respective mobile phases suggested by USP 2017. Assays were done and percent drug content was calculated using calibration curves.

TABLE 18

Assay results for each formulation (Rat studies)

| Sr. No. | Code | Formulation | Area (mAU*S) | Assay (%) |
|---|---|---|---|---|
| 1 | PA1 | Insulin glargine + chenodeoxycholic acid | 1664 | 105.2 |
| 2 | PA2 | Insulin glargine + labrasol | 1860 | 115.8 |
| 3 | PA1 | Octreotide acetate + chenodeoxycholic acid | 1638 | 24.5 |
| 4 | PA1 | Teriparatide + chenodeoxycholic acid | 2203 | 98.02 |
| 5 | PA3 | Teriparatide + piperine | 2385 | 106.1 |

Stability Studies of Insulin Glargine Capsules

TABLE 19

Insulin glargine Granules composition

| Sr. No | Ingredient | Quantity per capsule Batch I | Quantity per capsules Batch II |
|---|---|---|---|
| 1 | Insulin glargine | 0.12 mg | 0.12 mg |
| 2 | Chenodeoxycholic acid | 30 mg | — |
| 3 | Labrasol | — | 30 mg |
| 4 | Microcrystalline Cellulose | 15 mg | 20 mg |
| 5 | Croscarmellose Sodium | 2.5 mg | 1.5 mg |
| 6 | Mannitol | 2.38 mg | 5.38 mg |
| 7 | Binder (HPMCE-5) | Q.S. | Q.S |
| | Total weight | 50 mg | 50 mg |

Capsule Filling—

Mode: Manual filling; Size of capsule: 2; Weight of granules filled: as per above formula Storage of Capsules and Granules—

Temperature: 25±3° C.; Humidity: 35±5% RH; Container: HDPE 60 cc for capsules/clear glass vial with rubber closure for granules.

Observation:

From the equation (y=30.977x−292.26 obtained from HPLC data), content for Insulin glargine present in formulation was found to be 105.2% and 115.8% for batch I and batch II respectively.

Stability Studies (75 Days):

Both batches were stored at room temperature 25° C. for 85 days and assays were repeated.

Observation:

From the equation (y=30.977x−292.26 obtained from HPLC data), content for Insulin glargine present in formulation was found to be 97.25% and 91.63% for batch I and batch II respectively as can be seen from Table 20 below.

TABLE 20

Stability studies comparative analysis

| Formulation | Area (0 days) | Assay (0 days) | Area (85 days) | Assay (85 days) |
|---|---|---|---|---|
| Insulin glargine + Chenodeoxycholic acid (Batch I) | 1664 mAU*s | 105.2% | 1515.3 mAU*s | 97.25% |

TABLE 20-continued

Stability studies comparative analysis

| Formulation | Area (0 days) | Assay (0 days) | Area (85 days) | Assay (85 days) |
|---|---|---|---|---|
| Insulin glargine + Labrasol (Batch II) | 1860 mAU*s | 115.8% | 1410.9 mAU*s | 91.63% |

Stability studies of Teriparatide

TABLE 21

Teriparatide granules composition

| Sr. No | Ingredient | Quantity per capsule Batch I | Quantity per capsules Batch II |
|---|---|---|---|
| 1 | Teriparatide | 0.12 mg | 0.12 mg |
| 2 | Chenodeoxycholic acid | 30 mg | — |
| 3 | Piperine | — | 3 mg |
| 4 | Microcrystalline Cellulose | 15 mg | 20 mg |
| 5 | Croscarmellose Sodium | 2.5 mg | 1.5 mg |
| 6 | Mannitol | 2.38 mg | 5.38 mg |
| 7 | Binder (HPMCE-5) | Q.S. | Q.S |
|  | Total weight | 50 mg | 30 mg |

Capsule Filling—

Mode: Manual filling; Size of capsule: 2; Weight of granules filled: as per above formula Storage of Capsules and Granules—

Temperature: 25±3° C.; Humidity: 35±5% RH; Container: HDPE 60 cc for capsules/clear glass vial with rubber closure for granules Observation:

From the equation (y=18.924x−22.539 obtained from HPLC data), content for teriparatide acetate present in formulation was found to be 98.02% and 106% for batch I and batch II respectively.

Stability Studies (75 Days)—

Both batches were stored at room temperature 25° C. for 75 days and assays were repeated.

Observation:

From the equation (y=18.924x−22.539 obtained from HPLC data), content for teriparatide acetate present in formulation was found to be 92.88% and 89.76% for batch I and batch II respectively.

TABLE 22

Stability studies comparative analysis

| Formulation | Area (0 days) | Assay (0 days) | Area (75 days) | Assay (75 days) |
|---|---|---|---|---|
| Teriparatide + Chenodeoxycholic acid (Batch I) | 2203 mAU*s | 98.02% | 2087 mAU*s | 92.88% |
| Teriparatide + Piperine (Batch II) | 2385 mAU*s | 106.0% | 2016 mAU*s | 89.76% |

Assay Procedure—Leuprolide Acetate for Rat Studies

Calibration curve of leuprolide acetate was prepared using HPLC—About 112 mg and 104 mg of granules (equivalent to 100 µg) were weighed accurately and diluted with 1 mL of mobile phase; This gives us dispersion with theoretical concentration of 100 µg/mL for leuprolide acetate; The dispersion was vortexed for 2 minutes and then filtered through a 0.2 µm syringe filter; 20.0 µL of this filtered solution was then injected into the HPLC system to determine the peptide content. Observation: From the equation, y=42.67x−76.447 obtained from HPLC studies for the peptide, content for leuprolide acetate. % peptide content was found to be (A) leuprolide acetate+Labrasol ALF granules (PA 2): 97.45%; and (B) leuprolide acetate+Labrasol ALF+ Piperine granules (PA 2+3): 105.11%.

Dissolution Study of Leuprolide Capsules

Formulation Containing Labrasol ALF with Leuprolide (PA 2) was Selected for Dissolution Study (Based on Assay Results)

Set Up 1: Using Dialysis Membrane—

Medium: Phosphate buffer pH 6.80; Volume: 10 ml; Withdrawal volume: 400 µl; Stirring rate: 100 RPM; Granules filled: 140 mg (equivalent to 1 capsule); Dialysis membrane specification: HIMEDIA LM395-30MT; Pore size: 25 nm; Average flat width: 29.31 mm; Average diameter: 17.5 mm

TABLE 23

Release study of leuprolide using dialysis membrane

| Time | Area | % Release |
|---|---|---|
| 5 | 0 | Leuprolide not |
| 10 | 0 | released through |
| 15 | 0 | dialysis |
| 20 | 0 | membrane |
| 25 | 0 |  |

Set Up 2: Using Rotating Basket (USP TYPE 1)—

Medium: Phosphate buffer pH 6.80; Volume: 25 ml; Withdrawal volume: 400 µl; Stirring rate: 100 RPM; Granules filled: 140 mg in gelatin capsule.

TABLE 24

In vitro release data for set up 2

| Time (min) | Area | conc. (µg/ml) | conc. µg/0.5 ml | Error | conc. ug/25 ml | CDR | % CDR |
|---|---|---|---|---|---|---|---|
| 0 | 0 | 0 | 0 | 0 | 0 | 0 | 0 |
| 5 | 214.9 | 6.827911882 | 3.413955941 | 3.4139559 | 170.697797 | 174.111753 | 13.92894 |
| 10 | 400.76 | 11.18366534 | 5.591832669 | 5.5918327 | 279.5916335 | 285.183466 | 22.81468 |
| 15 | 279.59 | 8.343965315 | 4.171982658 | 13.177771 | 208.5991329 | 221.776904 | 17.74215 |
| 20 | 366.37 | 10.37771268 | 5.188856339 | 18.366628 | 259.442817 | 277.809445 | 22.22476 |
| 30 | 370.09 | 10.46489337 | 5.232446684 | 23.599074 | 261.6223342 | 285.221408 | 22.81771 |

TABLE 24-continued

In vitro release data for set up 2

| Time (min) | Area | conc. (μg/ml) | conc. μg/0.5 ml) | Error | conc. ug/25 ml) | CDR | % CDR |
|---|---|---|---|---|---|---|---|
| 45 | 330 | 9.525357394 | 4.762678697 | 28.361753 | 238.1339348 | 266.495688 | 21.31966 |
| 60 | 456.86 | 12.49840637 | 6.249203187 | 34.610956 | 312.4601594 | 347.071116 | 27.76569 |
| 90 | 321.25 | 9.320295289 | 4.660147645 | 39.271104 | 233.0073822 | 272.278486 | 21.78228 |

Set Up 3: Using Rotating Basket (USP TYPE 1)
Medium: Phosphate buffer pH 6.80; Volume: 30 ml; Withdrawal volume: 400 μl; Stirring rate: 500 RPM; Granules filled: 140 mg in gelatin capsule.

TABLE 25

In vitro release data for set up 3

| Time (min) | Area | conc. (μg/ml) | conc. μg/0.4 ml) | Error | conc. ug/30 ml) | CDR | % CDR |
|---|---|---|---|---|---|---|---|
| 0 | 0 | 0 | 0 | 0 | 0 | 0 | 0 |
| 5 | 229.95 | 7.180618702 | 2.872247481 | 2.8722475 | 215.418561 | 218.290809 | 17.46326 |
| 10 | 215.206 | 6.835083197 | 2.734033279 | 2.7340333 | 205.0524959 | 207.786529 | 16.62292 |
| 20 | 258.028 | 7.838645418 | 3.135458167 | 8.7417389 | 235.1593625 | 243.901101 | 19.51209 |
| 30 | 218.98 | 6.923529412 | 2.769411765 | 11.511151 | 207.7058824 | 219.217033 | 17.53736 |
| 45 | 236.02 | 7.322873213 | 2.929149285 | 14.4403 | 219.6861964 | 234.126496 | 18.73012 |
| 60 | 337.56 | 9.702531052 | 3.881012421 | 18.321312 | 291.0759316 | 309.397244 | 24.75178 |

Set Up 4: Using Rotating Basket (USP TYPE 1)
Medium: Phosphate buffer pH 6.80; Volume: 30 ml; Withdrawal volume: 400 μl; Stirring rate: 500 RPM; Granules filled: 140 mg in Hypromellose capsule (Size 0).

TABLE 26

In vitro release data for set up 4

| Time (min) | Area | conc. (μg/ml) | conc. (μg/0.4 ml) | Error | conc. (ug/30 ml) | CDR | % CDR |
|---|---|---|---|---|---|---|---|
| 0 | 0 | 0 | 0 | 0 | 0 | 0 | 0 |
| 5 | 0 | 1.791586595 | 0.716634638 | 0.7166346 | 53.74759784 | 54.4642325 | 4.357139 |
| 15 | 343.5 | 9.841738927 | 3.936695571 | 3.9366956 | 295.2521678 | 299.188863 | 23.93511 |
| 30 | 416.63 | 11.55558941 | 4.622235763 | 9.275566 | 346.6676822 | 355.943248 | 28.47546 |
| 45 | 527.55 | 14.15507382 | 5.662029529 | 14.937596 | 424.6522147 | 439.58981 | 35.16718 |
| 90 | 428.46 | 11.83283337 | 4.733133349 | 19.670729 | 354.9850012 | 374.65573 | 29.97246 |

Set Up 5: Using Rotating Basket (USP TYPE 1)
Medium: Phosphate buffer pH 6.80; Volume: 30 ml; Withdrawal volume: 500 μl; Stirring rate: 100 RPM; Granules filled: 140 mg without capsules directly in to the basket.

TABLE 27

In vitro release data for set up 5

| Time (min) | Area | conc. (μg/ml) | conc. μg/0.5 ml) | Error | Conc (ug/30 ml) | CDR | % CDR |
|---|---|---|---|---|---|---|---|
| 0 | 0 | 0 | 0 | 0 | 0 | 0 | 0 |
| 5 | 1491.97 | 36.7569018 | 18.3784509 | 18.378451 | 1102.707054 | 1121.08551 | 89.68684 |
| 10 | 1550.89 | 38.13773143 | 19.06886571 | 19.068866 | 1144.131943 | 1163.20081 | 93.05606 |
| 15 | 1280.8 | 31.80799156 | 15.90399578 | 53.351312 | 954.2397469 | 1007.59106 | 80.60728 |
| 20 | 1422 | 35.11710804 | 17.55855402 | 70.909866 | 1053.513241 | 1124.42311 | 89.95385 |

Set Up 6: Using Magnetic Stirrer
Medium: Phosphate buffer pH 6.80; Volume: 30 ml; Withdrawal volume: 500 µl; Stirring rate: 200 RPM; Granules filled: 140 mg in gelatin capsule size 2.

TABLE 28

In vitro release data for set up 6

| Time (min) | Area | conc. (µg/ml) | conc. µg/0.5 ml) | Error | conc. (ug/ 30 ml) | CDR | % CDR |
|---|---|---|---|---|---|---|---|
| 0 | 0 | 0 | 0 | 0 | 0 | 0 | 0 |
| 5 | 1761.8 | 43.08054839 | 21.5402742 | 21.540274 | 1292.416452 | 1313.95673 | 105.1165 |
| 10 | 1771.8 | 43.31490509 | 21.65745254 | 21.657453 | 1299.447153 | 1321.10461 | 105.6884 |
| 15 | 1750 | 42.8040075 | 21.40200375 | 64.59973 | 1284.120225 | 1348.71996 | 107.8976 |
| 20 | 1736.9 | 42.49700023 | 21.24850012 | 85.848231 | 1274.910007 | 1360.75824 | 108.8607 |

Set Up 7: Using Magnetic Stirrer
Medium: Phosphate buffer pH 6.80; Volume: 30 ml; Withdrawal volume: 500 µl; Stirring rate: 200 RPM; Granules filled: 140 mg in gelatin capsule size 2.

TABLE 29

In vitro release data for set up 7

| Time (min) | Area | conc. (µg/ml) | conc. µg/0.5 ml) | Error | conc. (ug/ 30 ml) | CDR | % CDR |
|---|---|---|---|---|---|---|---|
| 0 | 0 | 0 | 0 | 0 | 0 | 0 | 0 |
| 2.5 | 1440.6 | 35.55301148 | 17.77650574 | 17.776506 | 1066.590345 | 1084.36685 | 86.74935 |
| 5 | 1670.9 | 40.95024607 | 20.47512304 | 20.475123 | 1228.507382 | 1248.98251 | 99.9186 |
| 10 | 1603 | 39.35896414 | 19.67948207 | 57.931111 | 1180.768924 | 1238.70004 | 99.096 |
| 15 | 1638.4 | 40.18858683 | 20.09429341 | 78.025404 | 1205.657605 | 1283.68301 | 102.6946 |

Based on the data provided in Table 24 through 29, it could be noted that Leuprolide was not released from granules through dialysis membrane (Set up 1); Rotating basket (USP TYPE 1) was used for set up 2 and rotation of basket was not able to produce sufficient spinning motion to move/spin the material in medium and hence, the material along with gelatin settled down, ultimately affecting the release; Set up 3 was conducted by increasing RPM of basket (From 100 to 500), but even after increasing rpm of basket % CDR was found to be 24.75%; Set up 4 was conducted with increased RPM and replacing the gelatin capsule with Hypromellose capsule, wherein % CDR was found to be 29.97%; Set up 5 was performed in rotating basket without capsule, % CDR was found to be 90%, which confirms that material (Gelatin/Hypromellose) may increase the viscosity and retard the release of leuprolide from granules; Set up 6 and 7 were performed using magnetic stirrer in order to generate proper spinning of media throughout the analysis and the % CDR was found to be 108.8% and 102.6% respectively; all sets of experiments were conducted at 37° C. and change in temperature affect the disintegration of capsule, Disintegration time at 25° C. was 12 min and Disintegration time at 37° C. was less than 2 min.

Assay of Liraglutide Sodium Using HPLC
Trial 1:
Procedure: About 10.0 mg of granules both PA 2 (Table 16F) and PA 3+4 (Table 16G) were diluted with 10.0 mL of HPLC diluent (10% ACN in D.I water). This gives us dispersion with theoretical concentration of 74 µg/mL for Liraglutide sodium. The dispersion was sonicated for 5.0 minutes in an ultrasonic bath and then filtered through a 0.2 µm syringe filter. 20.0 µL of this filtered solution was then injected into the HPLC system to determine the peptide content. Observation: From the equation; y=79.283x−571.72 obtained from HPLC studies for the peptide, content for Liraglutide Sodium formulation with Labrasol ALF granules (PA 2) was found out to be 44.4% and 25.4% for Liraglutide Sodium formulation with Piperine and Solutol HS-15 (PA 3+4). (a) Liraglutide Sodium formulation with Piperine and Solutol HS-15 assay: 67.39% on vortex for 2 minutes; (b) Liraglutide Sodium formulation with Labrasol ALF granules assay: 80.43% on vortex for 2 minutes; (c) Liraglutide Sodium formulation with Piperine and Solutol HS-15 assay: 95.66% on vortex for 5 minutes; and (d) Liraglutide Sodium formulation with Labrasol ALF granules assay: 96.99% on vortex for 5 minutes.

Dissolution Study of Liraglutide
Medium: Phosphate buffer pH 6.80; Volume: 30 ml; Withdrawal volume: 500 µl; Stirring rate: 200 RPM.

TABLE 30

In vitro release data for liraglutide PA 2 (Table 16F)

| Time (min) | Area | conc (µg/ml) | conc (µg/1 ml) | Error | conc (ug/100 ml) | CDR | % CDR |
|---|---|---|---|---|---|---|---|
| 0 | 0 | 0 | 0 | 0 | 0 | 0 | 0 |
| 5 | 5050 | 70.90700402 | 35.45350201 | 35.45350201 | 7090.700402 | 7126.153904 | 59.38461587 |
| 7.5 | 5085.23 | 71.35136158 | 35.67568079 | 35.67568079 | 7135.136158 | 7170.811839 | 59.75676532 |

TABLE 30-continued

In vitro release data for liraglutide PA 2 (Table 16F)

| Time (min) | Area | conc (μg/ml) | conc (μg/1 ml) | Error | conc (ug/100 ml) | CDR | % CDR |
|---|---|---|---|---|---|---|---|
| 10 | 7804.21 | 105.6459771 | 52.82298853 | 123.9521713 | 10564.59771 | 10688.54988 | 89.07124899 |
| 15 | 9447.27 | 126.3699658 | 63.18498291 | 187.1371542 | 12636.99658 | 12824.13374 | 106.8677811 |
| 20 | 9912.43 | 132.2370496 | 66.11852478 | 253.255679 | 13223.70496 | 13476.96063 | 112.3080053 |
| 30 | 9912.43 | 132.2370496 | 66.11852478 | 319.3742038 | 13223.70496 | 13543.07916 | 112.858993 |

TABLE 31

In vitro release data for liraglutide PA 3 + 4 (Table 16G)

| Time (min) | Area | conc. (μg/ml) | conc. (μg/1 ml) | Error | Conc (ug/100 ml) | CDR | % CDR |
|---|---|---|---|---|---|---|---|
| 0 | 0 | 0 | 0 | 0 | 0 | 0 | 0 |
| 5 | 0 | 0 | 0 | 0 | 0 | 0 | 0 |
| 7.5 | 6823.8 | 93.2800222 | 46.6400111 | 46.6400111 | 9328.00222 | 9374.642231 | 78.12201859 |
| 10 | 7692.74 | 104.240001 | 52.1200005 | 98.7600116 | 10424.0001 | 10522.76011 | 87.6896676 |
| 15 | 7778.6 | 105.322957 | 52.6614785 | 151.4214901 | 10532.2957 | 10683.71719 | 89.03097659 |
| 20 | 7987.41 | 107.9566868 | 53.9783434 | 205.3998335 | 10795.66868 | 11001.06851 | 91.67557095 |
| 30 | 8131.53 | 109.7744788 | 54.88723938 | 260.2870729 | 10977.44788 | 11237.73495 | 93.64779125 |

Observation:

The % CDR was found to be 112.85% and 93.64% for Liraglutide PA 2 and PA 3+4, respectively. More than 50% liraglutide sodium was found to be released between 5-7 minutes.

Quantification of Glucose & Insulin Glargine Level in STZ Induced Diabetic Rat Plasma Glucose & insulin glargine levels in plasma were quantified after dosing several formulations of insulin glargine to mid-jejunum in STZ induced diabetic S.D. rats.

Test formulation I: Insulin glargine (Lantus®)—Appearance: Solution for injection in a prefilled pen; Concentration: 100 IU/ml; Storage condition: 2-8° C.; Dose: 0.2 U/kg; Route: SC.

Test formulation II: Insulin glargine Formulation—MIRA 1 (Reduced glutathione/Chromium Picolinate of Table 15A)+Permeation Enhancer 1 (PA 1 of Table 16A) (oral solution in TRIS buffer)—Dose: 1.7 U/animal; Route: mid-jejunum Test formulation III: Insulin glargine Formulation—PA 2 (of Table 16B) and MIRA 2 (Ascorbate Sodium/Vanadium Oxide of Table 15B) (oral solution in TRIS buffer) —Dose: 1.7 U/animal; Route: mid-jejunum.

Observations:

There was no mortality observed following subcutaneous and mid-jejunum administration of Insulin glargine. The clinical signs observed are normal. With respect to sampling time points, during dosing, the blood collection time points was at 0, 20, 40, 60, 120 and 150 minutes post dose. ~100 μl of blood was collected in a pre-filled Na-EDTA eppendorf, from retro-orbital sinus puncture. Blood was centrifuged at 5000 rpm, 5 min, 4° c. to obtain plasma. Glucose was measured immediately after blood collection using Glucometer.

TABLE 32

Effect of treatments with different formulations on STZ induced diabetic rats

| Groups | n | % inhibition (min) | | | | |
|---|---|---|---|---|---|---|
| | | 20 | 40 | 60 | 120 | 150 |
| Vehicle | 2 | 1.6 | −1.6 | −2.2 | −1.5 | −1.8 |
| STZ + Insulin glargine (0.2 U/kg) | 3 | 22.9 | 25.5 | 22 | 39 | 17.2 |
| STZ + Test Formulation II | 3 | −23.2 | −15.1 | −14.7 | −13.2 | −15.4 |
| STZ + Test Formulation III | 3 | −3.5 | −13.1 | 0.8 | 8.8 | 10 |

TABLE 33

Bioavailability of Insulin glargine

| Groups | n | AUC ± SEM |
|---|---|---|
| Vehicle | 2 | 67705 ± 2965 |
| STZ + Insulin glargine (0.2 U/kg) | 3 | 39408 ± 8561 |
| STZ + Test Formulation II | 3 | 80133 ± 5168 |
| STZ + Test Formulation III | 3 | 57315 ± 3474 |

ELISA Study

Source: Invitron Ltd, Cat. No. MBS495369

Principle: This Glargine ELISA is a two-site immunoassay, employing a monoclonal antibody immobilised on microtitre wells and a soluble antibody labelled with horseradish peroxidase (HRP). A plasma sample is incubated in the microtitre well together and, after a wash step, the antibody-HRP conjugate solution is added. A second incubation is followed by a further wash step to remove unbound antibody-HRP conjugate before measurement. A substrate for the enzyme is added to each well and after a short incubation a further reagent is added to terminate the reaction. The intensity of the colour developed in each well is quantified in a microtitre plate reader set to record transmitted light at a wavelength of 450 nm (Kit Protocol: Used manufacturer recommended protocol Cat. No. MBS495369)

Procedure: Bring all kit components and samples to room temperature before use. Assemble the required number of coated strips in the plate holder. Any strips not used immediately may be stored inside a sealed polythene bag with silica gel desiccant. Make sure to fill remaining spaces in the plate holder with uncoated strips to ensure uniform heat transfer during incubation. Pipette 100 μl Sample Buffer into each well. Pipette 25 μl Standard or Sample into the respective wells. It is recommended that all standards and samples are run in duplicate. Attach a plate sealer and incubate for 2 hours at Room Temperature (18-22° C.). Remove the plate sealer and perform 3 wash cycles with chilled* working strength Wash Buffer (300 μl each cycle) using an automatic plate washer. Pipette 100 μl working strength antibody conjugate into each well. Attach a plate sealer and incubate for a further 4 hr at 4° C. (2-8° C.). Remove the plate sealer and perform 3 wash cycles with chilled* working strength Wash Buffer using an automatic plate washer. Add 100 μl Substrate Solution to each well. Incubate for 15 minutes at room temperature (18-22° C.) in the dark. Add 100 μl Stop Solution to each well. Measure light transmission in a microtitre plate reader set to 450 nm and, if available, with a background subtraction measured at an OD of 620/650 nm. FIG. 1 illustrates a graph depicting conc. vs. time profile of insulin glargine (mU/L) from different formulations.

The test formulation Insulin glargine—MIRA 1 (Reduced glutathione/Chromium Picolinate) plus permeation enhancer 1 (PA 1) was found to exhibit relative bioavailability of 9.25% & the test formulation Insulin glargine—PA 2 and MIRA 2 (Ascorbate Sodium/Vanadium Oxide) was found to exhibit relative bioavailability of 28.86%.

Quantification of Leuprolide Level in Dog Plasma Using ELISA Kit

Reference Test Formulation: LUPRODEX (Depot)—

Concentration: Each vial contains 3.75 mg of leuprolide acetate; Date of manufacture: November 2017; Date of expiry: October 2020; Storage condition: Store at room temperature (below 25° C.). Don't freeze; No. of vials: 1 vial with diluent.

Test Formulation FB: MIRA 5 (Table 15E)+PA 2 (Table 16H)—

Appearance: Hard gelatine capsule with white cap and white body; Concentration: Each 300 mg capsule contains 1.25 mg of leuprolide acetate; Date of manufacture: 21 Apr. 2018; Date of expiry: NA; Storage condition: Store at room temperature (below 25° C.); No. of test item capsules: 70 capsules (1 bottle).

Test Formulation H: MIRA 2 (Table 15F)+PA 2+3 (Table 16I)—

Appearance: Hard gelatine capsule with white cap and white body; Concentration: Each 300 mg capsule contains 1.25 mg of leuprolide acetate; Date of manufacture: 19 Apr. 2018; Date of expiry: NA; Storage condition: Store at room temperature (below 25° C.); No. of test item capsules: 70 capsules (1 bottle).

TABLE 34

Study Design

| | No. of animals | Administration route | Formulation | Dose |
|---|---|---|---|---|
| Group 1 | 2 | Subcutaneous | Reference | Leuprorelin, as label (one implant at start of program) |
| Group 2 | 2 | Oral | Formulation H (MIRA 2) | Leuprorelin 1.25 mg, once a day one capsule for 30 days |
| Group 3 | 2 | Oral | Formulation FB (MIRA 5) | Leuprorelin 1.25 mg, once a day one capsule for 30 days |

During the period of dose administration, the dogs (*Canis familiaris*, Breed —Beagle) were fasted (water allowed) overnight for approx. 12 hours prior to and 4 hours post dose administration. After administration of drug, all animals were observed for adverse clinical signs up to 720 hours after dosing. Body weights of the dogs used in the study were recorded prior to dosing.

Sampling Time Points

Approximately 2 mL of blood sample from each dog for Subcutaneous and oral dosing were collected for the following time points: 0, 1, 2, 6, 12, 24, 48, 72, 96, 120, 240, 312, 360, 480 and 720 h (total 15 points) from the jugular vein into labelled K2EDTA coated tubes.

ELISA Study Details

Source: Cat. No. S-1174 (Des-Gly10, D-Leu6, Pro-NHEt9)-LHRH (Leuprolide); Kit Protocol: Used manufacturer recommended protocol (Cat. No. S1174)

Results:

The test formulation FB was found to exhibit relative bioavailability of 56.53% & the test formulation H was found to exhibit relative bioavailability of 16%.

Quantification of Liraglutide Level in Dog Plasma Using ELISA Kit

Test Formulation I: Liraglutide—

Appearance: Solution for injection in a prefilled pen; Concentration: 6 mg/ml; Date of manufacture: February 2017; Date of expiry: July 2019; Storage condition: 2-8° C.; Dose: 0.6 mg/dog; Route: SC.

Test Formulation II (FA): MIRA 5 (Table 15E)+PA 2 (Table 16F)—

Dose: 12 mg (one capsule)/dog; Route: Oral.

Test Formulation III (G): MIRA 5 (Table 15E)+PA 3+4 (Table 16G)—

Dose: 12 mg (one capsule)/dog; Route: Oral

TABLE 35

Study Design

| | No. of animals | Administration route | Formulation | Dose |
|---|---|---|---|---|
| Period 1 | 2 | Subcutaneous | Formulation I Liraglutide | 0.6 mg/dog |
| | | 4-5 days washout | | |
| Period 2 | 2 | Oral | Formulation II FA | 12 mg (one capsule)/dog |
| | | 4-5 days washout | | |
| Period 3 | 2 | Oral | Formulation III G | 12 mg (one capsule)/dog |

There was no mortality observed following subcutaneous and oral administration of Liraglutide. The clinical signs observed are normal. Body weights of the dogs used in the study were recorded prior to dosing. During the period of dose administration, the dogs (*Canis lupus familiaris*, Breed: Beagle) were fasted (water allowed) overnight for approx. 12 hours prior to and 4 hours post dose administration. During dosing, the blood collection time points was at 0, 20, 30, 60, 120, 180, 240, 480 minutes post dose. 2 ml of blood was collected from the jugular vein into labelled K2EDTA coated tubes. Glucose was measured immediately after blood collection using Glucometer.

ELISA Study Details

Source: Krishgen BioSystems, Cat. No. KBI5020 Ver2.0

Kit Protocol: Used manufacturer recommended protocol (Cat. No. KBI5020) Ver2.0—(1) Determine wells for diluted standard, blank and sample. Prepare 5 wells for standard points, 1 well for blank. Add 50 μL each of dilutions of standard (read Reagent Preparation), blank and samples into the appropriate wells, respectively. And then add 50 μL of Liraglutide-Biotin to each well immediately. Shake the plate gently (using a microplate shaker is recommended). Cover with a Plate sealer. Incubate for 1 hour at 37 C. Liraglutide-Biotin may appear cloudy. Warm to room temperature and mix gently until solution appears uniform. (2) Aspirate the solution and wash with 350 μL of 1× Wash Solution to each well using a squirt bottle, multi-channel pipette, manifold dispenser or autowasher, and let it sit for 1-2 minutes. Remove the remaining liquid from all wells completely by snapping the plate onto absorbent paper. Repeat 3 times. After the last wash, remove any remaining Wash Buffer by aspirating or decanting. Invert the plate and blot it against absorbent paper. (3) Add 100 μL of Streptavidin-HRP working solution to each well. Incubate for 30 minutes at 37° C. after covering it with the Plate sealer. (4) Repeat the aspiration/wash process for total 5 times as conducted in step 2. (5) Add 90 μL of Substrate Solution to each well. Cover with a new Plate sealer. Incubate for 10-20 minutes at 37 C (Don't exceed 30 minutes). Protect from light. The liquid will turn blue by the addition of Substrate Solution. (6) Add 50 μL of Stop Solution to each well. The liquid will turn yellow by the addition of Stop solution. Mix the liquid by tapping the side of the plate. If color change does not appear uniform, gently tap the plate to ensure thorough mixing. (7) Remove any drop of water and fingerprint on the bottom of the plate and confirm there is no bubble on the surface of the liquid. Then, run the microplate reader and conduct measurement at 450 nm immediately.

The test formulation FA (Mira 5 plus Liraglutide+Labrasol) was found to exhibit relative bioavailability of 3.82% & the test formulation G (Mira 5 plus Liraglutide+Solutol+Piperine) was found to exhibit relative bioavailability of 3.57%.

Quantification of Octreotide in Rat Plasma Using ELISA Kit

Test Formulation I: Octreotide—

Appearance: Solution for injection; Concentration: 0.1 mg/ml; Storage condition: 2-8° C.; Dose: 10 μg/kg; Route: SC.

Test Formulation II:

MIRA 3 (Table 15C)+PA 1 (Table 16C) to be dosed into distal small intestine (ileum) to anesthetized S.D. rat; Dose: 144 μg/animal; Route: distal small intestine (ileum). During the experiment, the animals were non-fasted.

TABLE 36

Study Design

| Groups | n | Description of dose |
|---|---|---|
| Octreotide | 3 | s.c. |
| MIRA 3 + PA 1 | 3 | MIRA3 & PA1 mixed with tris buffer (2 ml/kg) |

There was no mortality observed following subcutaneous and distal small intestine (ileum) administration of octreotide. The clinical signs observed are normal. During dosing, the blood collection time points were at 0, 7, 15, 30, 45, 60 and 90 min post dose. ~100 μl of blood was collected in a pre-filled Na-EDTA eppendorf, from retro-orbital sinus puncture. Blood was centrifuged at 5000 rpm, 5 min, 4° c. to obtain plasma.

ELISA study details

Source:

PeninsulaLaboratories International, Inc, Cat. No. S-1341.0001

Kit Protocol:

Used manufacturer recommended protocol (Cat. No. S-1341.0001)—Into each well of the immunoplate add 25 μl antiserum (in EIA buffer). Add 25 μl EIA buffer to blank wells; Incubate at room temperature for 1 hour; Add 50 μl standard or sample (in diluent). Do not wash plate before adding. Add 50 μl diluent to blank wells; Incubate at room temperature for 2 hours. Shorter preincubations may result in lower sensitivity; Rehydrate the Bt-tracer (in EIA buffer) and add 25 μl/well; Incubate at 4° C. overnight. For best results re-equilibrate to RT before proceeding; Wash immunoplate 5 times with 300 μl/well of EIA buffer. Be very careful not to cross-contaminate between wells in the first wash/dispensing cycle. In each wash cycle empty plate contents with a rapid flicking motion of the wrist, then gently blot dry the top of plate on paper towels. Dispense 300 μl of EIA buffer into each well and gently shake for at least a few seconds. Thorough washing is essential. Add 100 μl/well of streptavidin-HRP. Tap or centrifuge the SAHRP vial to collect all liquid contents on the bottom of the vial. Dilute 1/200 in EIA buffer (60 μl/12 ml) and vortex. Add 100 μl to all wells, including the blanks. Incubate at room temperature for 1 hour. Wash immunoplate 5 times (see step 7). Add 100 μl/well of TMB solution. Add to all wells, including the blanks. Incubate at room temperature (usually 30-60 minutes). You may read the developing blue color at 650 nm and use the data for your calculations. Terminate reactions by adding 100 μl 2 N HCl per well. Read absorbance at 450 nm within ten minutes.

The test formulation MIRA 3 (Uric Acid: Sodium Vanadate)+PA 1 was found to exhibit relative bioavailability of 0.41%.

Quantification of Teriparatide in Rat Plasma Using ELISA Kit

Test Formulation I:

Teriparatide; Appearance: Solution for injection; Concentration: 600 μg/2.4 ml; Storage condition: 2-8° C.; Dose: 10 μg/animal; Route: SC.

Test Formulation II:

MIRA 4 (Table 15D) plus PA1 (Table 16D) was dosed into distal small intestine (ileum) at a dose of 240 μg/animal to anesthetized rats; Dose: 240 μg/animal; Route: distal small intestine (ileum).

Test Formulation III:

MIRA 1 (Table 15A) plus PA3 (Table 16E) was dosed into distal small intestine (ileum) at a dose of 240 μg/animal to anesthetized S.D. rats; Dose: 240 μg/animal; Route: distal small intestine (ileum).

TABLE 37

Study Design

| Groups | n | Description of dose |
|---|---|---|
| Teriparatide | 3 | s.c. |
| MIRA 4 + PA 1 | 3 | MIRA4 & PA1 mixed with tris buffer (2 ml/kg) |
| MIRA 1 + PA 3 | 3 | MIRA1 & PA3 mixed with tris buffer (2 ml/kg) |

During the experiment, the animals were non-fasted. There was no mortality observed following subcutaneous and distal small intestine (ileum) administration of teriparatide. The clinical signs observed are normal. During dosing, the blood collection time points were at 0, 7, 15, 30, 45, 60 and 90 min post dose. ~100 μl of blood was collected in a pre-filled Na-EDTA eppendorf, from retro-orbital sinus puncture. Blood was centrifuged at 5000 rpm, 5 min, 4C temperature to obtain plasma.

ELISA Study Details

Source:

Immutopics Cat. No. 60-3900.

Kit Protocol:

Used manufacturer recommended protocol (Cat. No. 60-3900) —Place a sufficient number of Streptavidin Coated Strips in a holder to run PTH standards, controls and unknown samples; Pipet 150 μL of standard, control, or sample into the designated or mapped well. Freeze the remaining standards and controls as soon as possible after use; Pipet 50 μL of the Working Antibody Solution consisting of 1 part HRP Antibody and 1 part Biotinylated Antibody into each well; Cover the plate with one plate sealer and then cover with aluminum foil to avoid exposure to light; Incubate plate at room temperature for three (3) hours on a horizontal rotator set at 180-220 RPM; Remove the aluminum foil and plate sealer. Using an automated microtiter plate washer aspirate the contents of each well. Wash each well five times by dispensing 350 μL of working wash solution into each well and then completely aspirating the contents. A suitable aspiration device may also be used; Pipet 200 μL of ELISA HRP Substrate into each of the wells; Re-cover the plate with the plate sealer and aluminum foil. Incubate at room temperature for 30 minutes on a horizontal rotator set at 180-220 RPM; Remove the aluminum foil and plate sealer. Read the absorbance at 620 nm (see Note) within 5 minutes in a microtiter plate reader against the 0 pg/mL Standard wells as a blank; Immediately pipet 50 μL of ELISA Stop Solution into each of the wells. Mix on horizontal rotator for 1 minute; Read the absorbance at 450 nm within 10 minutes in a microtiter plate reader against a reagent blank of 200 μL of Substrate and 50 μL of Stop Solution; If dual wavelength correction is available set the Measurement wavelength to 450 nm and Reference wavelength to absorbance used in step #9.

The test formulation MIRA 4 (Ascorbate Sodium: Manganses Gluconate) plus PA 1 was found to exhibit relative bioavailability of 0.89%. The test formulation MIRA 1 (Reduced Glutathione/Chromium Picolinate) plus PA3 found to exhibit relative bioavailability of 0.89%.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Invention

The present disclosure provides a pharmaceutical composition that can overcomes the deficiencies associated with the prior art reported compositions.

The present disclosure provides a pharmaceutical composition for effective delivery of peptide.

The present disclosure provides a pharmaceutical composition for oral delivery of peptide.

The present disclosure provides a pharmaceutical composition that provides protection, at least in part, to the peptide from proteolytic degradation upon oral ingestion.

The present disclosure provides a pharmaceutical composition that increases bioavailability of peptide.

The present disclosure provides a pharmaceutical composition that is safe.

The present disclosure provides a pharmaceutical composition that is cost-effective, easy to prepare and with long shelf-life.

We claim:

1. A pharmaceutical composition comprising:
   a pharmaceutically effective amount of teriparatide; and
   a pharmaceutically acceptable amount of a combination of:
   (a) at least one metal in form of any or a combination of a salt thereof and a complex thereof; and
   (b) at least one reducing agent,
   wherein, said at least one metal is selected from any or a combination of: vanadium, chromium and manganese, and wherein said combination of (a) at least one metal in form of any or a combination of a salt and a complex and (b) at least one reducing agent affords protection, at least in part, to said teriparatide from proteolytic degradation upon ingestion thereof, and
   wherein said pharmaceutical composition further comprises at least one absorption enhancer
   wherein the pharmaceutical composition is in a unit dosage form and said teriparatide and said at least one metal in form of any or a combination of a salt thereof and a complex thereof are present in physically separated form in the unit dosage form.

2. The pharmaceutical composition as claimed in claim 1, wherein said at least one metal is vanadium and wherein the pharmaceutical composition comprises any or a combination of the salt of vanadium and the complex of vanadium in an amount ranging from about 0.01 mg to about 15 mg per unit dose.

3. The pharmaceutical composition as claimed in claim 2, wherein the any of the salt of vanadium and the complex of vanadium is selected independently from a group comprising: vanadium (V) oxide, sodium vanadate, vanadium sulfate, vanadyl sulfate, vanadium biguanide, bis(maltolato) oxavandium (IV), vanadium acetate, vanadyl picolinate and vanadyl citrate.

4. The pharmaceutical composition as claimed in claim 1, wherein said at least one metal is chromium and wherein the pharmaceutical composition comprises any or a combination of the salt of chromium and the complex of chromium in an amount ranging from about 0.02 mg to about 0.5 mg per unit dose.

5. The pharmaceutical composition as claimed in claim 4, wherein the any of the salt of chromium and the complex of chromium is selected independently from a group comprising: chromium picolinate, chromium polynicotinate, chromium nicotinate, chromium chloride and chromium acetate.

6. The pharmaceutical composition as claimed in claim 1, wherein said at least one metal is manganese and wherein the pharmaceutical composition comprises any or a combination of the salt of manganese and the complex of manganese in an amount ranging from about 0.1 mg to about 10 mg per unit dose.

7. The pharmaceutical composition as claimed in claim 6, wherein the any of the salt of manganese and the complex of manganese is selected independently from a group comprising: manganese gluconate, manganese sulfate, potassium permanganate and manganese chloride.

8. The pharmaceutical composition as claimed in claim 1, wherein said pharmaceutical composition is present in form of any of capsule-in-capsule and tablet-in-capsule.

9. The pharmaceutical composition as claimed in claim 1, wherein said at least one reducing agent is selected from any or a combination of ascorbic acid, reduced glutathione, cysteine, uric acid, reducing sugar, glyceraldehyde, α-tocopherol, vitamin A, α-lipoic acid, dihydro-α-lipoic acid, glucose, galactose, lactose, maltose, thiol-bearing compound, a thiorner and pharmaceutically acceptable salts thereof.

10. The pharmaceutical composition as claimed in claim 1, wherein said pharmaceutical composition comprises the at least one reducing agent in an amount ranging from about 1 mg to about 1000 mg per unit dose.

11. The pharmaceutical composition as claimed in claim 1, wherein said at least one absorption enhancer is present in an amount ranging from about 10 mg to about 1000 mg per unit dose.

12. The pharmaceutical composition as claimed in claim 1, wherein said pharmaceutical composition is formulated as any of a solid oral dosage form and a liquid oral dosage form, with proviso that when said pharmaceutical composition is formulated as the liquid oral dosage form, the pharmaceutical composition comprises water in an amount of less than about 5% v/v.

* * * * *